(12) United States Patent
Penner et al.

(10) Patent No.: US 8,148,083 B2
(45) Date of Patent: Apr. 3, 2012

(54) METHODS OF SCREENING FOR TRPM4 MODULATORS OF INSULIN SECRETION

(75) Inventors: Reinhold Penner, Honolulu, HI (US); Andrea Fleig, Honolulu, HI (US)

(73) Assignee: The Queen's Medical Center, Honolulu, HI (US)

( * ) Notice: Subject to any disclaimer, the term of this patent is extended or adjusted under 35 U.S.C. 154(b) by 540 days.

(21) Appl. No.: 11/753,914

(22) Filed: May 25, 2007

(65) Prior Publication Data

US 2008/0039336 A1    Feb. 14, 2008

Related U.S. Application Data

(60) Provisional application No. 60/808,767, filed on May 25, 2006.

(51) Int. Cl.
*G01N 33/53* (2006.01)
(52) U.S. Cl. .............................. 435/7.1; 435/4; 436/501
(58) Field of Classification Search ........................ None
See application file for complete search history.

(56) References Cited

U.S. PATENT DOCUMENTS

| | | | |
|---|---|---|---|
| 6,194,634 B1 * | 2/2001 | Seino et al. | 800/18 |
| 6,642,003 B2 | 11/2003 | Perfetti | |
| 6,849,708 B1 | 2/2005 | Habener | |
| 7,452,675 B2 * | 11/2008 | Penner et al. | 435/7.1 |
| 2002/0142377 A1 * | 10/2002 | Glucksmann et al. | 435/69.1 |

FOREIGN PATENT DOCUMENTS

WO    WO 9808979 A1 *  3/1998

OTHER PUBLICATIONS

Ashcroft FM, et al. "Glucose induces closure of single potassium channels in isolated rat pancreatic β-cells" *Nature*, 312, 446-8 (1984).
Barg S, et al. "A Subset of 50 Secretory Granules in Close Contact with L-Type $Ca^{2+}$ Channels Accounts for First-Phase Insulin Secretion in Mouse β- Cells" *Diabetes*, 51 Suppl 1, S74-82 (2002).
Berggren PO, et al. "Removal of $Ca^{2+}$ Channel $\beta_3$ Subunit Enchances $Ca^{2+}$ Oscillation Frequency and Insulin Exocytosis" *Cell*, 119, 273-84 (2004).
Bergsten P. "Role of Oscillatiosn in Membrane Potential, Cytoplasmic $Ca^{2+}$, and Metabolism for Plasma Insulin Oscillations" *Diabetes*, 51 Suppl 1, S171-6 (2002).
Cheng, et al. "TRPM4 Controls Insulin in Pancreatin Beta-cells", Cell Calcium, 2007, vol. 41, pp. 51-61.
Clapham DE. "TRP channels as cellular sensors" *Nature*, 426, 517-24 (2003).
Earley S, et al."Critical Role for Transient Receptor Potential channel TRPM4 in Myogenic Constriction of Cerebral Arteries" *Circ Res*, 95, 922-9 (2004).
Gilon P, et al. "Control Mechanismis of the Oscillatiosn of Insulin Secretion in Vitro and in Vivo" *Diabetes*, 51 Suppl 1, S144-51 (2002).
Göpel S, et al. "Voltage-gated and resting membrane currents recorded from B0cells in intact mouse pancreatic islets" *J Physiol*, 521 Pt 3, 717-28 (1999).
Guinamard R, et al. "Funcational Characterization of ca $Ca^{2+}$-activated non-selective cation channel in human atrial cardiomyocytes" *J Physiol*, 558, 75-83 (2004).
Harteneck C et al. "From worm to man: three subfamilies of TRP channels" *Trends Neurosci*, 23, 159-66.(2000).
Henquin JC. "Triggering and Amplyifying Pathways of Regulation of Insulin Secretion by Glucose" *Diabetes*, 49, 1751-60 (2000).
Launay P, et al. "*TRPM4 is a Ca2+-Activated Nonselective Cation Channel Mediating Cell Membrane Depolarization*" Cell, 109, 397-407 (2002).
Launay P, et al. "TRPM4 Regulates Calcium Oscillatiosn After T Cell Activation" *Science*, 306, 1374-7 (2004).
Lin JM, et al. "Pulsatile Insulin Release From Islets Isolated From Three Subjects With Type 2 Diabetes" *Diabetes*, 51, 988-93 (2002).
Montell C, et al. "A Unified Nomenclature for the Superfamily of TRP Cation Channels" *Mol Cell*, 9, 229-31(2002).
O'Rahilly S, et al. "Impaired pulsatile secretion of insulin in relatives of patients with non-insulin-dependent diabetes" *N Engl J Med*, 318, 1225-30 (1988).
Xu XZ, et al. "Regulation of melastatin, a TRP-related protein, through interaction with a cytoplasmic isoform" *Proc Natl Acad Sci U S A*, 98, 10692-7 (2001).

* cited by examiner

*Primary Examiner* — Christine J Saoud
*Assistant Examiner* — Jegatheesan Seharaseyon
(74) *Attorney, Agent, or Firm* — Morgan Lewis & Bockius LLP

(57) ABSTRACT

The invention relates to methods useful in identifying candidate agents that modulate insulin secretion from an insulin secreting cell, where such molecules modulate TRPM4 activity and expression in the insulin secreting cell.

6 Claims, 26 Drawing Sheets

```
ggtctggaag cagagccggc ggagggagcg ccggggccct gggctgcagg aggttgcggc   60
ggccgcggca gcatggtggt gccggagaag gagcagagct ggatccccaa gatcttcaag  120
aagaagacct gcacgacgtt catagttgac tccacagatc cgggagggac cttgtgccag  180
tgtgggcgcc cccggaccgc ccacccgca gtggccatgg aggatgcctt cggggcagcc   240
gtggtgaccg tgtgggacag cgatgcacac accacggaga agcccaccga tgcctacgga  300
gagctggact tcacgggggc cggccgcaag cacagcaatt tcctccggct ctctgaccga  360
acggatccag ctgcagttta tagtctggtc acacgcacat ggggcttccg tgccccgaac  420
ctggtggtgt cagtgctggg gggatcgggg ggccccgtcc tccagacctg gctgcaggac  480
ctgctgcgtc gtgggctggt gcgggctgcc cagagcacag gagcctggat tgtcactggg  540
ggtctgcaca cgggcatcgg ccggcatgtt ggtgtggctg tacgggacca tcagatggcc  600
agcactgggg gcaccaaggt ggtggccatg ggtgtggccc cctggggtgt ggtccggaat  660
agagacaccc tcatcaaccc caagggctcg ttccctgcga ggtaccggtg gcgcggtgac  720
ccggaggacg gggtccagtt tcccctggac tacaactact cggccttctt cctggtggac  780
gacggcacac acggctgcct gggggggcgag aaccgcttcc gcttgcgcct ggagtcctac  840
atctcacagc agaagacggg cgtgggaggg actggaattg acatccctgt cctgctcctc  900
ctgattgatg gtgatgagaa gatgttgacg cgaatagaga acgccaccca ggctcagctc  960
ccatgtctcc tcgtggctgg ctcaggggga gctgcggact gcctggcgga gaccctggaa 1020
gacactctgg ccccagggag tggggagcc aggcaaggcg aagcccgaga tcgaatcagg 1080
cgtttctttc ccaaagggga ccttgaggtc ctgcaggccc aggtggagag gattatgacc 1140
cggaaggagc tcctgacagt ctattcttct gaggatgggt ctgaggaatt cgagaccata 1200
gttttgaagg cccttgtgaa ggcctgtggg agctcggagg cctcagccta cctggatgag 1260
ctgcgtttgg ctgtggcttg gaaccgcgtg gacattgccc agagtgaact ctttcgggggg 1320
gacatccaat ggcggtcctt ccatctcgaa gcttccctca tggacgccct gctgaatgac 1380
cggcctgagt tcgtgcgctt gctcatttcc cacggcctca gcctgggcca cttcctgacc 1440
ccgatgcgcc tggcccaact ctacagcgcg gcgccctcca actcgctcat ccgcaacctt 1500
ttggaccagg cgtcccacag cgcaggcacc aaagccccag ccctaaaagg gggagctgcg 1560
gagctccggc cccctgacgt ggggcatgtg ctgaggatgc tgctggggaa gatgtgcgcg 1620
ccgaggtacc cctccggggg cgcctgggac cctcacccag gccagggctt cggggagagc 1680
atgtatctgc tctcggacaa ggccacctcg ccgctctcgc tggatgctgg cctcgggcag 1740
gcccccctgga gcgacctgct tctttgggca ctgttgctga acagggcaca gatggccatg 1800
tacttctggg agatgggttc caatgcagtt tcctcagctc ttggggcctg tttgctgctc 1860
cgggtgatgg cacgcctgga gcctgacgct gaggaggcag cacggaggaa agacctggcg 1920
ttcaagtttg aggggatggg cgttgacctc tttggcgagt gctatcgcag cagtgaggtg 1980
agggctgccc gcctcctcct ccgtcgctgc ccgctctggg gggatgccac ttgcctccag 2040
ctggccatgc aagctgacgc ccgtgccttc tttgcccagg atggggtaca gtctctgctg 2100
acacagaagt ggtggggaga tatggccagc actacaccca tctgggccct ggttctcgcc 2160
ttcttttgcc ctccactcat ctacacccgc ctcatcacct tcaggaaatc agaagaggag 2220
cccacacggg aggagctaga gtttgacatg gatagtgtca ttaatgggga agggcctgtc 2280
gggacggcgg acccagccga aagacgccg ctgggggtcc cgcgccagtc gggccgtccg 2340
ggttgctgcg ggggccgctg cgggggcgc cggtgcctac gccgctggtt ccacttctgg 2400
ggcgcgccgg tgaccatctt catgggcaac gtggtcagct acctgctgtt cctgctgctt 2460
ttctcgcggg tgctgctcgt ggatttccag ccggcgccgc cggctccct ggagctgctg 2520
ctctatttct gggctttcac gctgctgtgc gaggaactgc gccagggcct gagcggaggc 2580
gggggcagcc tcgccagcgg gggccccggg cctggccatg cctcactgag ccagcgcctg 2640
cgcctctacc tcgccgacag ctggaaccag tgcgacctag tggctctcac ctgcttcctc 2700
ctgggcgtgg gctgccggct gaccccgggt ttgtaccacc tgggccgcac tgtcctctgc 2760
atcgacttca tggttttcac ggtgcggctg cttcacatct tcacggtcaa aaacagctg 2820
gggcccaaga tcgtcatcgt gagcaagatg atgaaggacg tgttcttctt cctcttcttc 2880
ctcggcgtgt ggctggtagc ctatggcgtg ccacggaggg ggctcctgag gccacgggac 2940
```

FIG. 2A

```
agtgacttcc caagtatcct gcgccgcgtc ttctaccgtc cctacctgca gatcttcggg 3000
cagattcccc aggaggacat ggacgtggcc ctcatggagc acagcaactg ctcgtcggag 3060
cccggcttct gggcacaccc tcctggggcc caggcgggca cctgcgtctc ccagtatgcc 3120
aactggctgg tggtgctgct cctcgtcatc ttcctgctcg tggccaacat cctgctggtc 3180
aacttgctca ttgccatgtt cagttacaca ttcggcaaag tacagggcaa cagcgatctc 3240
tactggaagg cgcagcgtta ccgcctcatc cgggaattcc actctcggcc cgcgctggcc 3300
ccgcccttta tcgtcatctc ccacttgcgc ctcctgctca ggcaattgtg caggcgaccc 3360
cggagccccc agccgtcctc cccggccctc gagcatttcc gggtttacct ttctaaggaa 3420
gccgagcgga agctgctaac gtgggaatcg gtgcataagg agaactttct gctggcacgc 3480
gctagggaca agcgggagag cgactccgag cgtctgaagc gcacgtccca gaaggtggac 3540
ttggcactga aacagctggg acacatccgc gagtacgaac agcgcctgaa agtgctggag 3600
cgggaggtcc agcagtgtag ccgcgtcctg gggtgggtgg ccgaggccct gagccgctct 3660
gccttgctgc ccccaggtgg gccgccaccc cctgacctgc ctgggtccaa agactgagcc 3720
ctgctggcgg acttcaagga gaagccccca caggggattt tgctcctaga gtaaggctca 3780
tctgggcctc ggccccgca cctggtggcc ttgtccttga ggtgagcccc atgtccatct 3840
cggccactgt caggaccacc tttgggagtg tcatccttac aaaccacagc atgcccggct 3900
cctcccagaa ccagtcccag cctgggagga tcaaggcctg gatcccgggc cgttatccat 3960
ctggaggctg cagggtcctt ggggtaacag ggaccacaga cccctcacca ctcacagatt 4020
cctcacactg gggaaataaa gccatttcag aggaaaaaaa a                    4061
                                                        SEQ ID NO: 1
```

FIG. 2B

```
Met Val Val Pro Glu Lys Glu Gln Ser Trp Ile Pro Lys Ile Phe Lys
 1           5                   10                  15
Lys Lys Thr Cys Thr Thr Phe Ile Val Asp Ser Thr Asp Pro Gly Gly
            20                  25                  30
Thr Leu Cys Gln Cys Gly Arg Pro Arg Thr Ala His Pro Ala Val Ala
        35                  40              45
Met Glu Asp Ala Phe Gly Ala Ala Val Val Thr Val Trp Asp Ser Asp
 50                      55                  60
Ala His Thr Thr Glu Lys Pro Thr Asp Ala Tyr Gly Glu Leu Asp Phe
 65              70                  75                      80
Thr Gly Ala Gly Arg Lys His Ser Asn Phe Leu Arg Leu Ser Asp Arg
                85                  90                  95
Thr Asp Pro Ala Ala Val Tyr Ser Leu Val Thr Arg Thr Trp Gly Phe
            100             105             110
Arg Ala Pro Asn Leu Val Val Ser Val Leu Gly Gly Ser Gly Gly Pro
        115                 120             125
Val Leu Gln Thr Trp Leu Gln Asp Leu Leu Arg Arg Gly Leu Val Arg
    130             135                 140
Ala Ala Gln Ser Thr Gly Ala Trp Ile Val Thr Gly Gly Leu His Thr
145             150                 155                     160
Gly Ile Gly Arg His Val Gly Val Ala Val Arg Asp His Gln Met Ala
                165             170                 175
Ser Thr Gly Gly Thr Lys Val Val Ala Met Gly Val Ala Pro Trp Gly
            180             185                 190
Val Val Arg Asn Arg Asp Thr Leu Ile Asn Pro Lys Gly Ser Phe Pro
        195             200                 205
Ala Arg Tyr Arg Trp Arg Gly Asp Pro Glu Asp Gly Val Gln Phe Pro
    210             215                 220
Leu Asp Tyr Asn Tyr Ser Ala Phe Phe Leu Val Asp Asp Gly Thr His
225             230                 235                     240
Gly Cys Leu Gly Gly Glu Asn Arg Phe Arg Leu Arg Leu Glu Ser Tyr
                245                 250             255
Ile Ser Gln Gln Lys Thr Gly Val Gly Gly Thr Gly Ile Asp Ile Pro
            260             265             270
Val Leu Leu Leu Leu Ile Asp Gly Asp Glu Lys Met Leu Thr Arg Ile
        275             280             285
Glu Asn Ala Thr Gln Ala Gln Leu Pro Cys Leu Leu Val Ala Gly Ser
    290             295             300
Gly Gly Ala Ala Asp Cys Leu Ala Glu Thr Leu Glu Asp Thr Leu Ala
305             310             315                     320
Pro Gly Ser Gly Gly Ala Arg Gln Gly Glu Ala Arg Asp Arg Ile Arg
                325             330             335
Arg Phe Phe Pro Lys Gly Asp Leu Glu Val Leu Gln Ala Gln Val Glu
            340             345             350
Arg Ile Met Thr Arg Lys Glu Leu Leu Thr Val Tyr Ser Ser Glu Asp
        355             360             365
Gly Ser Glu Glu Phe Glu Thr Ile Val Leu Lys Ala Leu Val Lys Ala
    370             375             380
Cys Gly Ser Ser Glu Ala Ser Ala Tyr Leu Asp Glu Leu Arg Leu Ala
385             390             395                     400
```

*FIG. 3A*

```
Val Ala Trp Asn Arg Val Asp Ile Ala Gln Ser Glu Leu Phe Arg Gly
            405                 410                 415
Asp Ile Gln Trp Arg Ser Phe His Leu Glu Ala Ser Leu Met Asp Ala
        420                 425                 430
Leu Leu Asn Asp Arg Pro Glu Phe Val Arg Leu Leu Ile Ser His Gly
        435                 440                 445
Leu Ser Leu Gly His Phe Leu Thr Pro Met Arg Leu Ala Gln Leu Tyr
    450                 455                 460
Ser Ala Ala Pro Ser Asn Ser Leu Ile Arg Asn Leu Leu Asp Gln Ala
465             470                 475                 480
Ser His Ser Ala Gly Thr Lys Ala Pro Ala Leu Lys Gly Gly Ala Ala
                485                 490                 495
Glu Leu Arg Pro Pro Asp Val Gly His Val Leu Arg Met Leu Leu Gly
            500                 505                 510
Lys Met Cys Ala Pro Arg Tyr Pro Ser Gly Gly Ala Trp Asp Pro His
        515                 520                 525
Pro Gly Gln Gly Phe Gly Glu Ser Met Tyr Leu Leu Ser Asp Lys Ala
    530                 535                 540
Thr Ser Pro Leu Ser Leu Asp Ala Gly Leu Gly Gln Ala Pro Trp Ser
545             550                 555                 560
Asp Leu Leu Leu Trp Ala Leu Leu Leu Asn Arg Ala Gln Met Ala Met
                565                 570                 575
Tyr Phe Trp Glu Met Gly Ser Asn Ala Val Ser Ser Ala Leu Gly Ala
            580                 585                 590
Cys Leu Leu Leu Arg Val Met Ala Arg Leu Glu Pro Asp Ala Glu Glu
        595                 600                 605
Ala Ala Arg Arg Lys Asp Leu Ala Phe Lys Phe Glu Gly Met Gly Val
    610                 615                 620
Asp Leu Phe Gly Glu Cys Tyr Arg Ser Ser Glu Val Arg Ala Ala Arg
625             630                 635                 640
Leu Leu Leu Arg Arg Cys Pro Leu Trp Gly Asp Ala Thr Cys Leu Gln
                645                 650                 655
Leu Ala Met Gln Ala Asp Ala Arg Ala Phe Phe Ala Gln Asp Gly Val
            660                 665                 670
Gln Ser Leu Leu Thr Gln Lys Trp Trp Gly Asp Met Ala Ser Thr Thr
        675                 680                 685
Pro Ile Trp Ala Leu Val Leu Ala Phe Phe Cys Pro Pro Leu Ile Tyr
    690                 695                 700
Thr Arg Leu Ile Thr Phe Arg Lys Ser Glu Glu Pro Thr Arg Glu
705             710                 715                 720
Glu Leu Glu Phe Asp Met Asp Ser Val Ile Asn Gly Glu Gly Pro Val
            725                 730                 735
Gly Thr Ala Asp Pro Ala Glu Lys Thr Pro Leu Gly Val Pro Arg Gln
        740                 745                 750
Ser Gly Arg Pro Gly Cys Cys Gly Arg Cys Gly Gly Arg Arg Cys
    755                 760                 765
Leu Arg Arg Trp Phe His Phe Trp Gly Ala Pro Val Thr Ile Phe Met
    770                 775                 780
Gly Asn Val Val Ser Tyr Leu Leu Phe Leu Leu Leu Phe Ser Arg Val
785                 790                 795                 800
Leu Leu Val Asp Phe Gln Pro Ala Pro Pro Gly Ser Leu Glu Leu Leu
                805                 810                 815
```

FIG. 3B

```
Leu Tyr Phe Trp Ala Phe Thr Leu Leu Cys Glu Glu Leu Arg Gln Gly
            820             825                 830
Leu Ser Gly Gly Gly Gly Ser Leu Ala Ser Gly Gly Pro Gly Pro Gly
        835             840             845
His Ala Ser Leu Ser Gln Arg Leu Arg Leu Tyr Leu Ala Asp Ser Trp
850             855                 860
Asn Gln Cys Asp Leu Val Ala Leu Thr Cys Phe Leu Leu Gly Val Gly
865             870             875                     880
Cys Arg Leu Thr Pro Gly Leu Tyr His Leu Gly Arg Thr Val Leu Cys
                885             890                     895
Ile Asp Phe Met Val Phe Thr Val Arg Leu Leu His Ile Phe Thr Val
                900             905             910
Asn Lys Gln Leu Gly Pro Lys Ile Val Ile Val Ser Lys Met Met Lys
        915             920             925
Asp Val Phe Phe Phe Leu Phe Phe Leu Gly Val Trp Leu Val Ala Tyr
    930             935             940
Gly Val Ala Thr Glu Gly Leu Leu Arg Pro Arg Asp Ser Asp Phe Pro
945             950             955                     960
Ser Ile Leu Arg Arg Val Phe Tyr Arg Pro Tyr Leu Gln Ile Phe Gly
            965             970             975
Gln Ile Pro Gln Glu Asp Met Asp Val Ala Leu Met Glu His Ser Asn
            980             985             990
Cys Ser Ser Glu Pro Gly Phe Trp Ala His Pro Pro Gly Ala Gln Ala
        995             1000            1005
Gly Thr Cys Val Ser Gln Tyr Ala Asn Trp Leu Val Val Leu Leu Leu
        1010            1015            1020
Val Ile Phe Leu Leu Val Ala Asn Ile Leu Leu Val Asn Leu Leu Ile
1025            1030            1035                    1040
Ala Met Phe Ser Tyr Thr Phe Gly Lys Val Gln Gly Asn Ser Asp Leu
                1045            1050            1055
Tyr Trp Lys Ala Gln Arg Tyr Arg Leu Ile Arg Glu Phe His Ser Arg
            1060            1065            1070
Pro Ala Leu Ala Pro Pro Phe Ile Val Ile Ser His Leu Arg Leu Leu
            1075            1080            1085
Leu Arg Gln Leu Cys Arg Arg Pro Arg Ser Pro Gln Pro Ser Ser Pro
        1090            1095            1100
Ala Leu Glu His Phe Arg Val Tyr Leu Ser Lys Glu Ala Glu Arg Lys
1105            1110            1115                    1120
Leu Leu Thr Trp Glu Ser Val His Lys Glu Asn Phe Leu Leu Ala Arg
                1125            1130            1135
Ala Arg Asp Lys Arg Glu Ser Asp Ser Glu Arg Leu Lys Arg Thr Ser
                1140            1145            1150
Gln Lys Val Asp Leu Ala Leu Lys Gln Leu Gly His Ile Arg Glu Tyr
        1155            1160            1165
Glu Gln Arg Leu Lys Val Leu Glu Arg Glu Val Gln Gln Cys Ser Arg
        1170            1175            1180
Val Leu Gly Trp Val Ala Glu Ala Leu Ser Arg Ser Ala Leu Leu Pro
1185            1190            1195                    1200
Pro Gly Gly Pro Pro Pro Asp Leu Pro Gly Ser Lys Asp
            1205            1210
```
                                                                SEQ ID: 2

FIG. 3C

PCR: TRPM4

IB: Anti-TRPM4

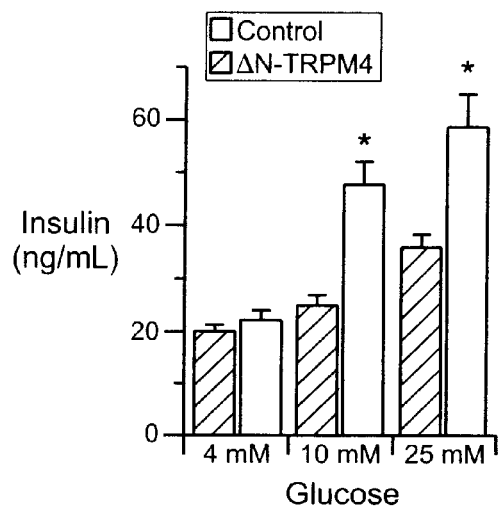
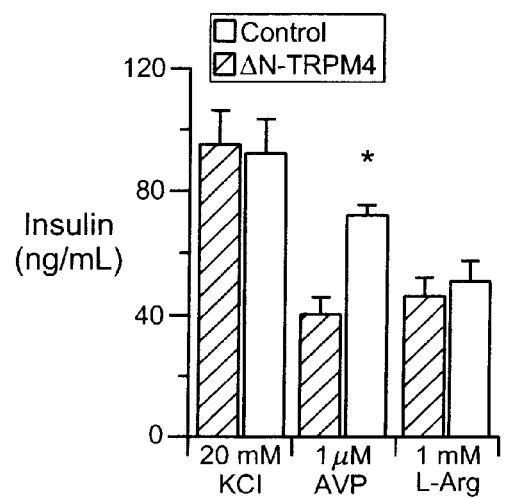
FIG. 5A
FIG. 5B
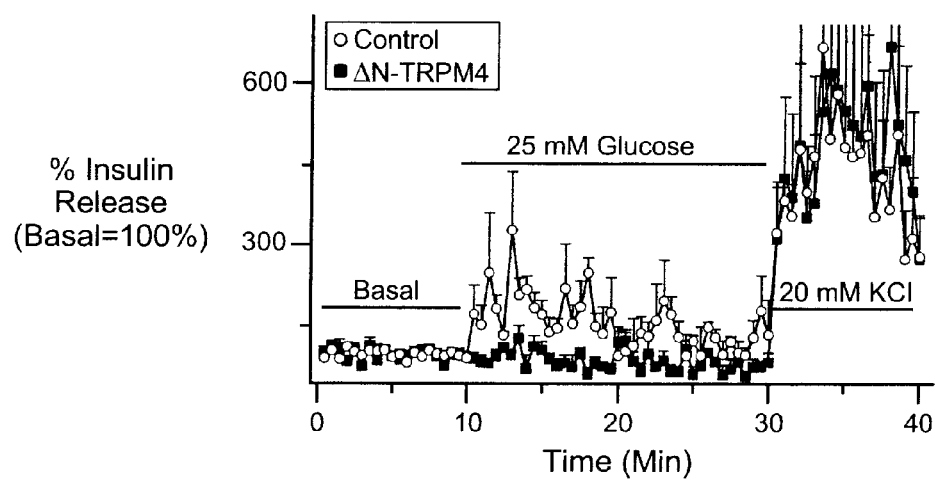
FIG. 5C

SEQUENCE LISTING

<160> NUMBER OF SEQ ID NOS: 2

<210> SEQ ID NO 1
<211> LENGTH: 4061
<212> TYPE: DNA
<213> ORGANISM: Homo sapiens

<400> SEQUENCE: 1

```
ggtctggaag cagagccggc ggagggagcg ccggggccct gggctgcagg aggttgcggc      60
ggccgcggca gcatggtggt gccggagaag gagcagagct ggatcccaa gatcttcaag      120 aagaagacct gcacgacgtt catagttgac tccacagatc cgggagggac cttgtgccag     180
tgtgggcgcc cccggaccgc ccaccccgca gtggccatgg aggatgcctt cggggcagcc     240
gtggtgaccg tgtgggacag cgatgcacac accacggaga agcccaccga tgcctacgga     300
gagctggact tcacggggc cggccgcaag cacagcaatt cctccggct ctctgaccga      360 acggatccag ctgcagttta tagtctggtc acacgcacat ggggcttccg tgccccgaac     420
ctggtggtgt cagtgctggg gggatcgggg ggccccgtcc tccagacctg gctgcaggac     480
ctgctgcgtc gtgggctggt gcgggctgcc cagagcacag gagcctggat tgtcactggg     540
ggtctgcaca cggcatcgg ccggcatgtt ggtgtggctg tacgggacca tcagatggcc     600
agcactgggg gcaccaaggt ggtggccatg ggtgtggccc ctggggtgt ggtccggaat      660 agagacaccc tcatcaaccc caagggctcg ttccctgcga gtaccggtg gcgcggtgac      720 ccggaggacg gggtccagtt tccctggac tacaactact cggccttctt cctggtggac      780
gacggcacac acggctgcct ggggggcgag aaccgcttcc gcttgcgcct ggagtcctac     840
atctcacagc agaagacggg cgtgggaggg actggaattg acatccctgt cctgctcctc     900
ctgattgatg gtgatgagaa gatgttgacg cgaatagaga cgccaccca ggctcagctc     960 ccatgtctcc tcgtggctgg ctcaggggga gctgcggact gcctggcgga gaccctggaa    1020
gacactctgg ccccaggag tggggagcc aggcaaggcg aagcccgaga tcgaatcagg      1080
cgtttctttc ccaagggga ccttgaggtc ctgcaggccc aggtggagag gattatgacc     1140
cggaaggagc tcctgacagt ctattcttct gaggatgggt ctgaggaatt cgagaccata    1200
gttttgaagg cccttgtgaa ggcctgtggg agctcggagg cctcagccta cctggatgag    1260
ctgcgtttgg ctgtggcttg gaaccgcgtg gacattgccc agagtgaact ctttcggggg    1320
gacatccaat ggcggtcctt ccatctcgaa gcttccctca tggacgccct gctgaatgac    1380
cggcctgagt tcgtgcgctt gctcatttcc cacggcctca gcctgggcca cttcctgacc    1440
ccgatgcgcc tggcccaact ctacagcgcg gcgcccccca actcgctcat ccgcaacctt    1500
ttggaccagg cgtcccacag cgcaggcacc aaagcccag ccctaaaagg ggagctgcg      1560 gagctccggc cccctgacgt ggggcatgtg ctgaggatgc tgctggggaa gatgtgcgcg    1620
ccgaggtacc cctccggggg cgcctgggac cctcacccag gccagggctt cggggagagc    1680
atgtatctgc tctcggacaa ggccaccctcg ccgctctcgc tggatgctgg cctcgggcag   1740
gcccctggaa gcgacctgct tctttgggca ctgttgctga acagggcaca gatggccatg    1800
tacttctggg agatgggttc caatgcagtt tcctcagctc ttggggcctg tttgctgctc    1860
cgggtgatgg cacgcctgga gcctgacgct gaggaggcag cacggaggaa agacctggcg    1920
ttcaagtttg aggggatggg cgttgacctc tttggcgagt gctatcgcag cagtgaggtg    1980
agggctgccc gcctcctcct ccgtcgctgc ccgctctggg gggatgccac ttgcctccag   2040
```

```
ctggccatgc aagctgacgc ccgtgccttc tttgcccagg atggggtaca gtctctgctg    2100
acacagaagt ggtggggaga tatggccagc actacaccca tctgggccct ggttctcgcc    2160
ttcttttgcc ctccactcat ctacacccgc ctcatcacct tcaggaaatc agaagaggag    2220
cccacacggg aggagctaga gtttgacatg gatagtgtca ttaatgggga agggcctgtc    2280
gggacggcgg acccagccga gaagacgccg ctggggtcc cgcgccagtc gggccgtccg     2340
ggttgctgcg ggggccgctg cggggggcgc cggtgcctac gccgctggtt ccacttctgg    2400
ggcgcgccgg tgaccatctt catgggcaac gtggtcagct acctgctgtt cctgctgctt    2460
ttctcgcggg tgctgctcgt ggatttccag ccggcgccgc ccggctccct ggagctgctg    2520
ctctatttct gggctttcac gctgctgtgc gaggaactgc gccagggcct gagcggaggc    2580
gggggcagcc tcgccagcgg ggggcccggg cctggccatg cctcactgag ccagcgcctg    2640
cgcctctacc tcgccgacag ctggaaccag tgcgacctag tggctctcac ctgcttcctc    2700
ctgggcgtgg gctgccggct gaccccgggt tgtaccacc tgggccgcac tgtcctctgc     2760
atcgacttca tggttttcac ggtgcggctg cttcacatct tcacggtcaa caaacagctg    2820
gggcccaaga tcgtcatcgt gagcaagatg atgaaggacg tgttcttctt cctcttcttc    2880
ctcggcgtgt ggctggtagc ctatggcgtg ccacggagg ggctcctgag gccacgggac     2940
agtgacttcc caagtatcct gcgccgcgtc ttctaccgtc cctacctgca gatcttcggg    3000
cagattcccc aggaggacat ggacgtggcc ctcatggagc acagcaactg ctcgtcggag    3060
cccggcttct gggcacaccc tcctggggcc caggcgggca cctgcgtctc ccagtatgcc    3120
aactggctgg tggtgctgct cctcgtcatc ttcctgctcg tggccaacat cctgctggtc    3180
aacttgctca ttgccatgtt cagttacaca ttcggcaaag tacagggcaa cagcgatctc    3240
tactggaagg cgcagcgtta ccgcctcatc cgggaattcc actctcggcc cgcgctggcc    3300 ccgccctta tcgtcatctc ccacttgcgc ctcctgctca ggcaattgtg caggcgaccc     3360
cggagccccc agccgtcctc cccggccctc gagcatttcc gggtttacct ttctaaggaa    3420
gccgagcgga agctgctaac gtgggaatcg gtgcataagg agaactttct gctggcacgc    3480
gctagggaca gcggggagag cgactccgag cgtctgaagc gcacgtccca gaaggtggac    3540
ttggcactga aacagctggg acacatccgc gagtacgaac agcgcctgaa agtgctggag    3600
cgggaggtcc agcagtgtag ccgcgtcctg gggtgggtgg ccgaggccct gagccgctct    3660
gccttgctgc cccaggtgg gccgccaccc cctgacctgc ctgggtccaa agactgagcc     3720
ctgctggcgg acttcaagga gaagccccca caggggattt tgctcctaga gtaaggctca    3780
tctgggcctc ggcccccgca cctggtggcc ttgtccttga ggtgagcccc atgtccatct    3840
gggccactgt caggaccacc tttgggagtg tcatccttac aaaccacagc atgcccggct    3900
cctcccagaa ccagtcccag cctggaggga tcaaggcctg gatcccgggc cgttatccat    3960
ctggaggctg cagggtcctt ggggtaacag ggaccacaga cccctcacca ctcacagatt    4020
cctcacactg gggaaataaa gccatttcag aggaaaaaaa a                        4061
```

<210> SEQ ID NO 2
<211> LENGTH: 1214
<212> TYPE: PRT
<213> ORGANISM: Homo sapiens

```
<400> SEQUENCE: 2

Met Val Val Pro Glu Lys Glu Gln Ser Trp Ile Pro Lys Ile Phe Lys
1               5                   10                  15

Lys Lys Thr Cys Thr Thr Phe Ile Val Asp Ser Thr Asp Pro Gly Gly
            20                  25                  30

Thr Leu Cys Gln Cys Gly Arg Pro Arg Thr Ala His Pro Ala Val Ala
        35                  40                  45

Met Glu Asp Ala Phe Gly Ala Val Val Thr Val Trp Asp Ser Asp
50                  55                  60

Ala His Thr Thr Glu Lys Pro Thr Asp Ala Tyr Gly Glu Leu Asp Phe
65                  70                  75                  80

Thr Gly Ala Gly Arg Lys His Ser Asn Phe Leu Arg Leu Ser Asp Arg
                85                  90                  95

Thr Asp Pro Ala Ala Val Tyr Ser Leu Val Thr Arg Thr Trp Gly Phe
            100                 105                 110

Arg Ala Pro Asn Leu Val Val Ser Val Leu Gly Gly Ser Gly Gly Pro
        115                 120                 125

Val Leu Gln Thr Trp Leu Gln Asp Leu Leu Arg Arg Gly Leu Val Arg
130                 135                 140

Ala Ala Gln Ser Thr Gly Ala Trp Ile Val Thr Gly Gly Leu His Thr
145                 150                 155                 160

Gly Ile Gly Arg His Val Gly Val Ala Val Arg Asp His Gln Met Ala
                165                 170                 175

Ser Thr Gly Gly Thr Lys Val Val Ala Met Gly Val Ala Pro Trp Gly
            180                 185                 190

Val Val Arg Asn Arg Asp Thr Leu Ile Asn Pro Lys Gly Ser Phe Pro
        195                 200                 205

Ala Arg Tyr Arg Trp Arg Gly Asp Pro Glu Asp Gly Val Gln Phe Pro
210                 215                 220

Leu Asp Tyr Asn Tyr Ser Ala Phe Phe Leu Val Asp Asp Gly Thr His
225                 230                 235                 240

Gly Cys Leu Gly Gly Glu Asn Arg Phe Arg Leu Arg Leu Glu Ser Tyr
                245                 250                 255

Ile Ser Gln Gln Lys Thr Gly Val Gly Gly Thr Gly Ile Asp Ile Pro
            260                 265                 270

Val Leu Leu Leu Leu Ile Asp Gly Asp Glu Lys Met Leu Thr Arg Ile
        275                 280                 285

Glu Asn Ala Thr Gln Ala Gln Leu Pro Cys Leu Leu Val Ala Gly Ser
290                 295                 300

Gly Gly Ala Ala Asp Cys Leu Ala Glu Thr Leu Glu Asp Thr Leu Ala
305                 310                 315                 320

Pro Gly Ser Gly Gly Ala Arg Gln Gly Glu Ala Arg Asp Arg Ile Arg
                325                 330                 335

Arg Phe Phe Pro Lys Gly Asp Leu Glu Val Leu Gln Ala Gln Val Glu
            340                 345                 350

Arg Ile Met Thr Arg Lys Glu Leu Leu Thr Val Tyr Ser Ser Glu Asp
        355                 360                 365

Gly Ser Glu Glu Phe Glu Thr Ile Val Leu Lys Ala Leu Val Lys Ala
370                 375                 380

Cys Gly Ser Ser Glu Ala Ser Ala Tyr Leu Asp Glu Leu Arg Leu Ala
385                 390                 395                 400

Val Ala Trp Asn Arg Val Asp Ile Ala Gln Ser Glu Leu Phe Arg Gly
                405                 410                 415
```

```
Asp Ile Gln Trp Arg Ser Phe His Leu Glu Ala Ser Leu Met Asp Ala
            420                 425                 430

Leu Leu Asn Asp Arg Pro Glu Phe Val Arg Leu Leu Ile Ser His Gly
        435                 440                 445

Leu Ser Leu Gly His Phe Leu Thr Pro Met Arg Leu Ala Gln Leu Tyr
    450                 455                 460

Ser Ala Ala Pro Ser Asn Ser Leu Ile Arg Asn Leu Leu Asp Gln Ala
465                 470                 475                 480

Ser His Ser Ala Gly Thr Lys Ala Pro Ala Leu Lys Gly Gly Ala Ala
                485                 490                 495

Glu Leu Arg Pro Pro Asp Val Gly His Val Leu Arg Met Leu Leu Gly
            500                 505                 510

Lys Met Cys Ala Pro Arg Tyr Pro Ser Gly Gly Ala Trp Asp Pro His
        515                 520                 525

Pro Gly Gln Gly Phe Gly Glu Ser Met Tyr Leu Leu Ser Asp Lys Ala
    530                 535                 540

Thr Ser Pro Leu Ser Leu Asp Ala Gly Leu Gly Gln Ala Pro Trp Ser
545                 550                 555                 560

Asp Leu Leu Leu Trp Ala Leu Leu Asn Arg Ala Gln Met Ala Met
                565                 570                 575

Tyr Phe Trp Glu Met Gly Ser Asn Ala Val Ser Ser Ala Leu Gly Ala
            580                 585                 590

Cys Leu Leu Leu Arg Val Met Ala Arg Leu Glu Pro Asp Ala Glu Glu
        595                 600                 605

Ala Ala Arg Arg Lys Asp Leu Ala Phe Lys Phe Glu Gly Met Gly Val
    610                 615                 620

Asp Leu Phe Gly Glu Cys Tyr Arg Ser Ser Glu Val Arg Ala Ala Arg
625                 630                 635                 640

Leu Leu Leu Arg Arg Cys Pro Leu Trp Gly Asp Ala Thr Cys Leu Gln
                645                 650                 655

Leu Ala Met Gln Ala Asp Ala Arg Ala Phe Phe Ala Gln Asp Gly Val
            660                 665                 670

Gln Ser Leu Leu Thr Gln Lys Trp Trp Gly Asp Met Ala Ser Thr Thr
        675                 680                 685

Pro Ile Trp Ala Leu Val Leu Ala Phe Phe Cys Pro Pro Leu Ile Tyr
    690                 695                 700

Thr Arg Leu Ile Thr Phe Arg Lys Ser Glu Glu Pro Thr Arg Glu
705                 710                 715                 720

Glu Leu Glu Phe Asp Met Asp Ser Val Ile Asn Gly Glu Gly Pro Val
                725                 730                 735

Gly Thr Ala Asp Pro Ala Glu Lys Thr Pro Leu Gly Val Pro Arg Gln
            740                 745                 750

Ser Gly Arg Pro Gly Cys Cys Gly Arg Cys Gly Arg Arg Cys
        755                 760                 765

Leu Arg Arg Trp Phe His Phe Trp Gly Ala Pro Val Thr Ile Phe Met
    770                 775                 780

Gly Asn Val Val Ser Tyr Leu Leu Phe Leu Leu Leu Phe Ser Arg Val
785                 790                 795                 800

Leu Leu Val Asp Phe Gln Pro Ala Pro Gly Ser Leu Glu Leu Leu
                805                 810                 815

Leu Tyr Phe Trp Ala Phe Thr Leu Leu Cys Glu Glu Leu Arg Gln Gly
            820                 825                 830

Leu Ser Gly Gly Gly Gly Ser Leu Ala Ser Gly Gly Pro Gly Pro Gly
        835                 840                 845
```

-continued

```
His Ala Ser Leu Ser Gln Arg Leu Arg Leu Tyr Leu Ala Asp Ser Trp
            850                 855                 860

Asn Gln Cys Asp Leu Val Ala Leu Thr Cys Phe Leu Leu Gly Val Gly
865                 870                 875                 880

Cys Arg Leu Thr Pro Gly Leu Tyr His Leu Gly Arg Thr Val Leu Cys
                    885                 890                 895

Ile Asp Phe Met Val Phe Thr Val Arg Leu Leu His Ile Phe Thr Val
                900                 905                 910

Asn Lys Gln Leu Gly Pro Lys Ile Val Ile Val Ser Lys Met Met Lys
            915                 920                 925

Asp Val Phe Phe Phe Leu Phe Phe Leu Gly Val Trp Leu Val Ala Tyr
    930                 935                 940

Gly Val Ala Thr Glu Gly Leu Leu Arg Pro Arg Asp Ser Asp Phe Pro
945                 950                 955                 960

Ser Ile Leu Arg Arg Val Phe Tyr Arg Pro Tyr Leu Gln Ile Phe Gly
                    965                 970                 975

Gln Ile Pro Gln Glu Asp Met Asp Val Ala Leu Met Glu His Ser Asn
                980                 985                 990

Cys Ser Ser Glu Pro Gly Phe Trp Ala His Pro Pro Gly Ala Gln Ala
            995                 1000                1005

Gly Thr Cys Val Ser Gln Tyr Ala Asn Trp Leu Val  Val Leu Leu
    1010                1015                1020

Leu Val Ile Phe Leu Leu Val  Ala Asn Ile Leu Leu  Val Asn Leu
    1025                 1030                1035

Leu Ile Ala Met Phe Ser Tyr  Thr Phe Gly Lys Val  Gln Gly Asn
    1040                 1045                1050

Ser Asp Leu Tyr Trp Lys Ala  Gln Arg Tyr Arg Leu  Ile Arg Glu
    1055                 1060                1065

Phe His Ser Arg Pro Ala Leu  Ala Pro Pro Phe Ile  Val Ile Ser
    1070                 1075                1080

His Leu Arg Leu Leu Leu Arg  Gln Leu Cys Arg Arg  Pro Arg Ser
    1085                 1090                1095

Pro Gln Pro Ser Ser Pro Ala  Leu Glu His Phe Arg  Val Tyr Leu
    1100                 1105                1110

Ser Lys Glu Ala Glu Arg Lys  Leu Leu Thr Trp Glu  Ser Val His
    1115                 1120                1125

Lys Glu Asn Phe Leu Leu Ala  Arg Ala Arg Asp Lys  Arg Glu Ser
    1130                 1135                1140

Asp Ser Glu Arg Leu Lys Arg  Thr Ser Gln Lys Val  Asp Leu Ala
    1145                 1150                1155

Leu Lys Gln Leu Gly His Ile  Arg Glu Tyr Glu Gln  Arg Leu Lys
    1160                 1165                1170

Val Leu Glu Arg Glu Val Gln  Gln Cys Ser Arg Val  Leu Gly Trp
    1175                 1180                1185

Val Ala Glu Ala Leu Ser Arg  Ser Ala Leu Leu Pro  Pro Gly Gly
    1190                 1195                1200

Pro Pro Pro Pro Asp Leu Pro  Gly Ser Lys Asp
    1205                 1210
```

US 8,148,083 B2

METHODS OF SCREENING FOR TRPM4 MODULATORS OF INSULIN SECRETION

CROSS-REFERENCE TO RELATED APPLICATIONS

This application claims the benefit under 35 U.S.C. §119(e) of U.S. Ser. No. 60/808,767, filed May 25, 2006, hereby incorporated by reference in its entirety.

STATEMENT REGARDING FEDERALLY SPONSORED RESEARCH OR DEVELOPMENT

This invention was made with government support from NIH grants R01AI046734 and R01050200. The government has certain rights in the invention.

FIELD OF THE INVENTION

The present invention relates to methods of screening for TRPM4 modulates that affect insulin of a novel family of Calcium-Activated Nonselective ("CAN") transmembrane channel polypeptides designated herein as "TRPM4".

BACKGROUND OF THE INVENTION

The Transient Receptor Potential (TRP) proteins are a family of ion channels which are divided into three major subfamilies: The TRPC "Canonical", the TRPV "Vanilloid", and the TRPM "Melastatin" (see Clapham D E. *Nature*, 426, 517-24 (2003) Harteneck C et al. *Trends Neurosci*, 23, 159-66.(2000), Montell C, et al. *Mol Cell*, 9, 229-31(2002)). The TRPM subfamily consists of eight members and information regarding their physiological function has just begun to surface. TRPM4 is a widely expressed calciumactivated nonselective cation (CAN) channel that conducts mainly $Na^+$ and $K^+$ without appreciable permeation to $Ca^{2+}$. It has a single channel conductance of ~25 pS and is directly activated by $[Ca^{2+}]_i$. Two splice variants have been described, a short form, which lacks 174 amino acid residues at the N-terminus (Xu XZ, et al. *Proc Natl Acad Sci U S A*, 98, 10692-7 (2001)) and a long (full-length) form (Launay P, et al. *Cell*, 109, 397-407 (2002)). In non-excitable cells such as T-lymphocytes, the TRPM4-mediated depolarization reduces the driving force for $Ca^{2+}$ entry through $Ca^{2+}$ Release-Activated $Ca^{2+}$ channels (CRAC) with significant impact on $Ca^{2+}$ oscillations and cytokine production (Launay P, et al. *Science*, 306, 1374-7 (2004)). TRPM4 is also implicated in myogenic constriction and cardiac function (Earley S, et al. *Circ Res*, 95, 922-9 (2004); Guinamard R, et al. *Physiol*, 558, 75-83 (2004)), suggesting that it may critically regulate $Ca^{2+}$ entry mechanisms in electrically excitable cells as well.

Changes in membrane potential during glucose stimulation are crucial for determining the shape and frequency of $Ca^{2+}$ oscillations in β-cells, because each depolarization induces a concomitant rise in the $[Ca^{2+}]_i$, that triggers insulin secretion (Bergsten P. *Diabetes*, 51 Suppl 1, S171-6 (2002); Gilon P, et al. *Diabetes*, 51 Suppl 1, S144-51 (2002)) Impaired $Ca^{2+}$ oscillations result in deficiencies in insulin secretion in certain forms of type 2 diabetes in humans and rodents (Henquin J C. *Diabetes*, 49, 1751-60 (2000); Lin J M, et al. *Diabetes*, 51, 988-93 (2002); O'Rahilly S, et al. *N Engl J Med* 318, 1225-30 (1988). The cellular and molecular components involved in membrane depolarization of β-cells have not been fully identified. Glucose stimulates insulin secretion by activating two pathways (Henquin J C. (2000). The triggering pathway involves a sequence of events beginning with glucose uptake, its metabolism and increase in ATP-ADP ratio, followed by closure of ATP-sensitive K+ (KATP) channels. Closure of KATP channels triggers membrane depolarization with opening of voltage-dependent calcium channels (VDCC's) and $Ca^{2+}$ influx (Ashcroft F M, et al. Nature, 312, 446-8 (1984)), however, this requires the additional presence of a depolarizing current that so far has not been identified. The opening of VDCC's is dependent on the cell membrane potential, which is around −70 mV at rest. Depolarization activates VDCC's, with peak $Ca^{2+}$ currents around 0 mV (Barg S, et al. Diabetes, 51 Suppl 1, S74-82 (2002); Berggren P O, et al. Cell, 119, 273-84 (2004); Gopel S, et al. J Physiol, 521 Pt 3, 717-28 (1999). TRPM4 currents reverse around 0 mV, and enhanced channel activity depolarizes cells from negative resting membrane potentials (launay P, et al. Cell, 109, 397-407 (2002)). The amplifying pathway, also referred to as the KATP-independent pathway, depends on an already elevated [Ca2+]i. I acts by increasing the efficiency of Ca2+ on secretion.

The global diabetes epidemic has resulted in a need for agents that can treat the symptoms of this illness. Of crucial importance in controlling diabetes is the ability to control and modulate insulin levels in the blood. Accordingly, the present invention provides methods for screening for candidate agents which can modulate insulin secretion from insulin secreting cells.

SUMMARY

In one aspect, methods are provided for screening for modulators of insulin secretion which includes the steps of contacting an insulin secreting cell with a candidate agent and detecting modulation of TRPM4 channel activity. In a preferred aspect modulation of TRPM4 channel activity is an indication that the candidate agent is a modulator of insulin secretion.

In another aspect, the methods screen for modulators of insulin secretion in which a cell expressing a TRPM4 channel is provided and candidate agent(s) which modulate that TRPM4 channel are identified. Such methods further comprise the steps of contacting one or more of those candidate agents with an insulin secreting cell and measuring the insulin secretion of the insulin secreting cell in response to the candidate agent(s).

In still another aspect, the methods screen for modulators of insulin secretion which involve the steps of contacting an insulin secreting cell with a candidate agent, detecting modulation of TRPM4 channel activity, and detecting modulation of insulin secretion.

In yet another aspect, the methods for identifying modulators of insulin secretion use a first pool of candidate agents and a first cell expressing a TRPM4 channel are provided. The first cell is contacted with one or more members of the first pool of candidate agents and the members of the first pool of candidate agents which modulate TRPM4 channel activity form a second pool of candidate agents. A second cell, which is an insulin secreting cell, is then contacted with the second pool of candidate agents, and members of the second pool of candidate agents which modulate insulin secretion of the second cell are identified.

The methods can also be used to screen for modulators of TRPM4. The method comprises contacting a cell expressing TRPM4 with a candidate agent and detecting modulation of TRPM4 channel activity. The cell can be an insulin secreting cell.

BRIEF DESCRIPTION OF THE DRAWINGS

FIG. 1A depicts the schematic and primary structure of TRPM4 with amino-terminal unique region 1-4 (ATU), transmembrane domain regions (TM), coiled-coil region (CC). Underlined amino acids represent the N-terminal extension of TRPM4; the rest of the sequence is identical to the short splicing variant TRPM4. The amino acid sequence of TRPM4 protein from amino acids 1 through 1214 (SEQ ID NO:2) is also shown. FIG. 1B depicts the Northern blot analysis of RNA from various tissues and human cell lines using a specific TRPM4 antisense RNA probe. Cell lines represent monocytes (U937), B lymphocytes (Ramos), T lymphocytes (Jurkat), basophils (Ku812), melanoma cells (G361) and embryonic kidney cells (HEK-293).

FIG. 2 shows the recombinant nucleic acid molecule of a TRPM4 cDNA comprised of nucleic acid sequences from 1 through about 4061 (SEQ ID NO: 1).

FIG. 3 shows the amino acid sequence of a recombinant TRPM4 protein comprised of sequences from 1 through about 1214 (SEQ ID NO: 2).

FIGS. 5A-C show TRPM4 suppression affects insulin secretion.

DETAILED DESCRIPTION

Figure 1A:
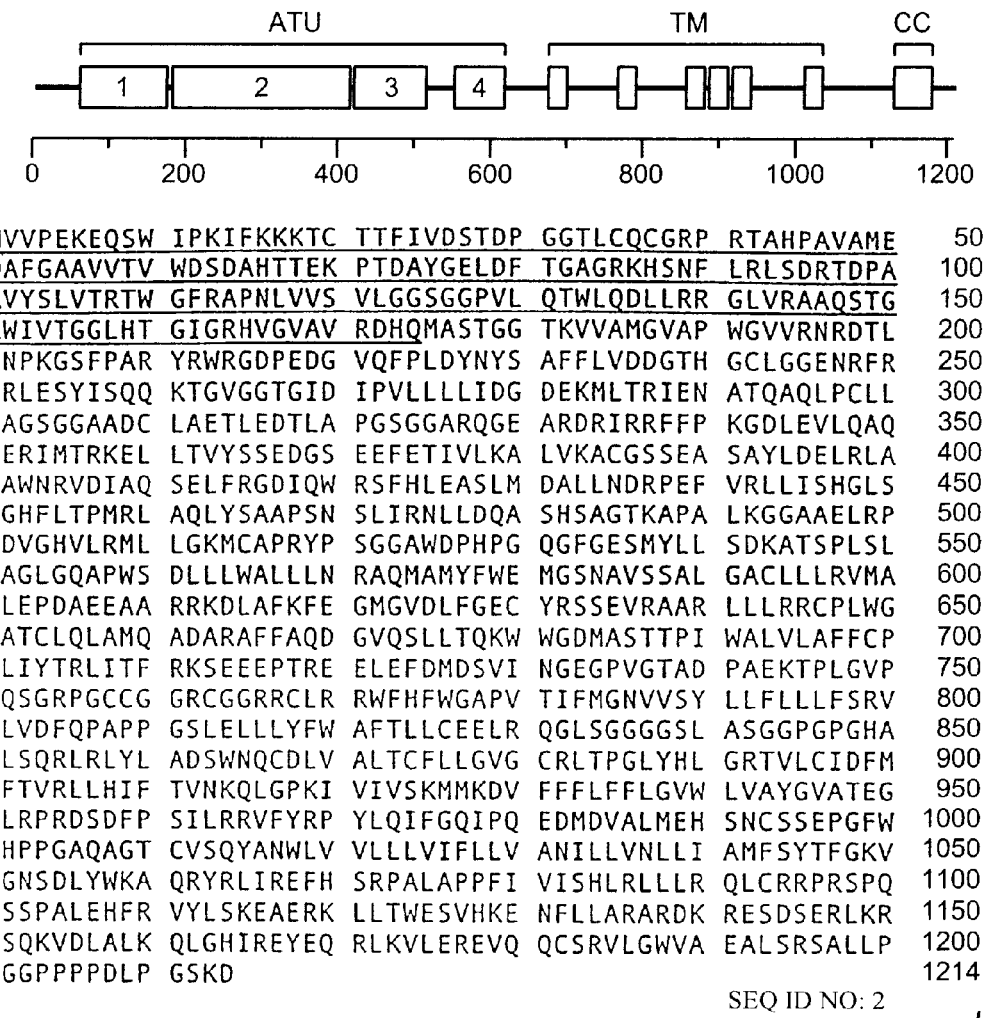
FIGS. 1A-B show the molecular characterization of TRPM4.
Figure 1B:
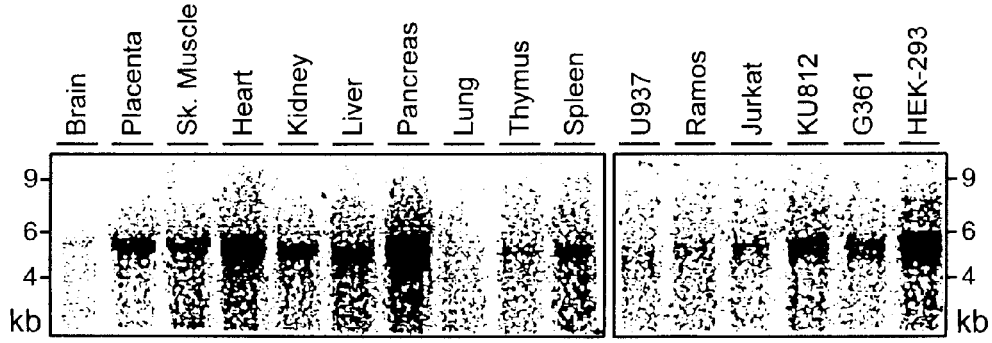

TRPM4 is not only abundantly expressed in β-cells, but critically regulates glucose-induced insulin secretion and suppression of TRPM4 by a dominant negative construct of TRPM4 suppresses the normal pulsatile pattern of insulin secretion (Cheng et al., Cell Calcium 41(1):51-61 (2007)). Translocation of TRPM4-containing vesicles via $Ca^{2+}$-dependent exocytosis also represents a mechanism by which β-cells regulate the pool of TRPM4 channels in the plasma membrane.

As described herein, the term "TRPM4" refers to a member of a family of $Ca^{2+}$ regulated transmembrane channel polypeptides previously known as the LTRPC family. The specific sequence disclosed herein as SEQ ID NO: 2 (FIG. 3) was derived from human kidney cells. TRPM4 is widely expressed in human tissues, with a dominant expression in the heart, placenta, and pancreas, as well as in the cell lines of the human hematopoetic system.

As described herein, "TRPM4 activity" refers to functional properties of the TRPM4 channel, including: activation by elevations in cytoplasmic $Ca^{2+}$ in the nanomolar range, gating by $Ca^{2+}$, conduction of monovalent cations such as $Na^+$, $K^+$, and $Cs^+$ without significant $Ca^{2+}$ permeation, activation subsequent to receptor-mediated $Ca^{2+}$-mobilization, regulation of $Ca^{2+}$-influxes by modulation of membrane potential and, in this manner, the driving force for $Ca^{2+}$ entry through other $Ca^{2+}$-permeable pathways, an absence of regulation by a voltage or $Ca^{2+}$-dependent inactivation, as well as the expression of the protein and its intracellular translocation.

TRPM4 channels are show a distinct activity from the "SOC" (Store Operated Channels) and "CRAC" (Calcium Release Activated Channels) polypeptides and channels, disclosed in "Characterization of a Calcium Family," WO 00/40614, the disclosure of which is expressly incorporated herein by reference. The SOC and CRAC proteins "may be activated upon depletion of $Ca^{2+}$ from intracellular calcium stores" (see WO 00/40614 at page 2) and are further "subject to inhibition by high levels of intracellular calcium" (see WO 00/40614 at page 10). Conversely, TRPM4 channels of the invention exhibit enhanced activity in the presence of high intracellular levels of calcium, may be directly gated by cytosolic $Ca^{2+}$ concentrations in the nanomolar range, decrease the driving force for $Ca^{2+}$ influx through store operated $Ca^{2+}$ channels of non-excitable cells, are not influenced by depletion or reduction of intracellular calcium stores, and operate to depolarize cell membranes in a $Ca^{2+}$-dependent manner. SOC and CRAC are not regulated in this manner.

TRPM4 can be derived from natural sources or recombinantly modified to make TRPM4 variants. The term "TRPM4 sequence" specifically encompasses naturally-occurring truncated or secreted forms (e.g., an extracellular domain sequence), naturally-occurring variant forms (e.g., alternatively spliced forms) and naturally-occurring allelic variants. The native sequence of the TRPM4 polypeptide from human kidney cells is a full-length or mature native sequence TRPM4 polypeptide comprising amino acids from 1 through about 1214 of SEQ ID NO:2 (FIG. 3).

The TRPM4 polypeptide of the invention, or a fragment thereof, also includes polypeptides having at least about 80% amino acid sequence identity, more preferably at least about 85% amino acid sequence identity, even more preferably at least about 90% amino acid sequence identity, and most preferably at least about 95% sequence identity with the amino acid sequence of SEQ ID NO:2. Such TRPM4 polypeptides include, for instance, TRPM4 polypeptides wherein one or more amino acid residues are substituted and/or deleted, at the N- or C-terminus, as well as within one or more internal domains, of the sequence of SEQ ID NO:2. Those skilled in the art will appreciate that amino acid changes may alter post-translational processes of the TRPM4 polypeptide variant, such as changing the number or position of glycosylation sites or altering the membrane anchoring characteristics. All TRPM4 proteins, however, exhibit one or more of the novel properties of the TRPM4 polypeptides as defined herein.

"Percent (%) amino acid sequence identity" with respect to the TRPM4 polypeptide sequences identified herein is defined as the percentage of amino acid residues in a candidate sequence that are identical with the amino acid residues of SEQ ID NO:2 (FIG. 3), after aligning the sequences and introducing gaps, if necessary, to achieve the maximum percent sequence identity, and not considering any conservative substitutions as part of the sequence identity. The % identity values used herein are generated by WU-BLAST-2 which was obtained from Altschul et al., Methods in Enzymology, 266:460-480 (1996); http.://blast.wustl/edu/blast/README .html. WU-BLAST-2 uses several search parameters, most of which are set to the default values. The adjustable parameters are set with the following values: overlap span=1 overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a further embodiment, the % identity values used herein are generated using a PILEUP algorithm. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351-360 (1987); the method is similar to that described by Higgins & Sharp *CABIOS* 5:151-153 (1989). Useful PILEUP parameters including a default gap weight of 3.00, a default gap length weight of 0.10, and weighted end gaps.

In yet another embodiment, TRPM4 polypeptides from humans or from other organisms may be identified and isolated using oligonucleotide probes or degenerate polymerase chain reaction (PCR) primer sequences with an appropriate genomic or cDNA library. As will be appreciated by those in the art, the TRPM4 unique nucleic acid sequence comprising nucleotide sequences of SEQ ID NO:1 (FIG. 2) encoding amino acids 1-174 of SEQ ID NO:2 (FIG. 3) or portions thereof, is particularly useful as a probe and/or PCR primer sequence. As is generally known in the art, preferred PCR primers are from about 15 to about 35 nucleotides in length, with from about 20 to about 30 being preferred, and may contain inosine as needed. The conditions for the PCR reaction are well known in the art.

In a preferred embodiment, TRPM4 is a "recombinant protein" which is made using recombinant techniques, i.e. through the expression of a recombinant TRPM4 nucleic acid in a cell line such as HEK293 cells. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constitutine at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a protein from one organism in a different organism or host cell. Alternatively, the protein may be made at a significantly higher concentration than is normally seen, through the use of an inducible promoter or high expression promoter such that the protein is made at increased concentration levels. Alternatively, the protein may be in a form not normally found in nature, as in the addition of an epitope tag or of amino acid substitutions, additions and deletions, as discussed below.

In a further embodiment, TRPM4 variants may be recombinantly engineered by replacing one amino acid with another amino acid having similar structural and/or chemical properties, such as the replacement of a leucine with a serine, i.e., conservative amino acid replacements.

In a further embodiment substitutions, deletions, additions or any combination thereof may be used to make TRPM4 variants. Generally these changes are done on a few amino acids to minimize the alteration of the molecule, although larger changes can often be tolerated. When small alterations in the characteristics of the TRPM4 polypeptide are desired, substitutions are generally made in accordance with the following Table 1:

TABLE 1

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

In a further embodiment, substantial changes in function or in immunological identity can be made by selecting substitutions that are less conservative than those shown in Chart 1. For example, substitutions may be made which more significantly affect the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g., leucyl, isoleucyl, phenylalanyl, valyl or alanyl; (b) a cysteine or proline is substituted for (or by) any other residue; (e) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine. The TRPM4 variants of this embodiment exhibit one or more properties of the TRPM4 polypeptides as described herein.

In a further embodiment, the variants typically exhibit the same qualitative biological activity and will elicit the same immune response as the naturally-occurring analogue, although variants can also be selected to modify the characteristics of the TRPM4 polypeptides. Alternatively, the variants may be designed such that the biological activity of TRPM4 is altered. For example, glycosylation sites may be altered or removed.

As used herein, "TRPM4 nucleic acids" or their grammatical equivalents, refer to nucleic acids, that encode TRPM4 polypeptides exhibiting one or more of the novel TRPM4 polypeptide properties previously described. The TRPM4 nucleic acids exhibit sequence homology to SEQ ID NO: 1 (FIG. 2) where homology is determined by comparing sequences or by hybridization assays.

A TRPM4 nucleic acid encoding a TRPM4 polypeptide is homologous to the cDNA forth in FIG. 2 (SEQ ID NO:1). Such TRPM4 nucleic acids are preferably greater than about 75% homologous, more preferably greater than about 80%, more preferably greater than about 85% and most preferably greater than 90% homologous. In some embodiments the homology will be as high as about 93 to 95 or 98%. Homology in this context means sequence similarity or identity, with identity being preferred. A preferred comparison for homology purpose is to compare the sequence containing sequencing differences to the known TRPM4 sequence. This homology will be determined using standard techniques known in the art, including, but not limited to, the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *PNAS USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wiss.), the Best Fit sequence program described by Devereux et al., *Nucl. Acid Res.* 12:387-395 (1984), preferably using the default settings, or by inspection.

In a preferred embodiment, "percent (%) nucleic acid sequence identity" is defined as the percentage of nucleotide residues in a candidate sequence that are identical with the nucleotide residue sequences of SEQ ID NO:1 (FIG. 2). A preferred method utilizes the BLASTN module of WU-BLAST-2 set to the default parameters, with overlap span and overlap fraction set to 1 and 0.125, respectively.

As described above, the TRPM4 nucleic acids can also be defined by homology as determined through hybridization studies. Hybridization is measured under low stringency conditions, more preferably under moderate stringency conditions, and most preferably, under high stringency conditions. The proteins encoded by such homologous nucleic acids exhibit at least one of the novel TRPM4 polypeptide properties defined herein. Thus, for example, nucleic acids which hybridize under high stringency to a nucleic acid having the sequence set forth as SEQ ID NO:1 (FIG. 2) and their complements, are considered TRPM4 nucleic acid sequences providing they encode a protein having a TRPM4 property.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional examples of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory, Manual*, New York: Cold Spring Harbor Press, 1989, and include the use of washing solution and hybridization conditions (e.g., temperature, ionic strength and %SDS) less stringent that those described above. An example of moderately stringent conditions is overnight incubation at 37° C. in a solution comprising: 20% formamide, 5×SSC (150 mM NaCl, 15 mM trisodium citrate). 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like. Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other sats at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

In another embodiment, less stringent hybridization conditions are used; for example, moderate or low stringency conditions may be used, as are known in the art. For additional details regarding stringency of hybridization reactions, see Ausubel el al., *Current Protocols in Molecular Biology*, Wiley Interscience Publishers, (1995).

The TRPM4 nucleic acids, as defined herein, may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also include the complement of the sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

By the term "recombinant nucleic acid" herein is meant nucleic acid, originally formed in vitro, in general, by the manipulation of nucleic acid by polymerases and endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Homologs and alleles of the TRPM4 nucleic acid molecules are included in the definition.

TRMP4 sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, BLAST, BLAST2 and INHERIT which employ various algorithms to measure homology, as has been previously described.

Nucleic acid encoding TRPM4 polypeptides, as defined herein, may be obtained by screening selected cDNA or genomic libraries using all or part of the nucleotide sequences of SEQ ID NO:1 (FIG. 2). Conventional primer extension procedures as described in Sambrook et al., supra, are used to detect precursors and processing intermediates of mRNA that may not have been reverse-transcribed into cDNA.

In another embodiment, the TRPM4 nucleic acid sequence of SEQ ID NO:1 (FIG. 2), as described above, is a cDNA fragment of a larger gene, i.e. it is a nucleic acid segment. "Genes" in this context include coding regions, non-coding regions, and mixtures of coding and non-coding regions. Accordingly, as will be appreciated by those in the art, using the sequences provided herein, additional sequences of TRPM4 genes can be obtained, using techniques well known in the art for cloning either longer sequences or the full length sequences; see Maniatis et al., and Ausubel, et al., supra, hereby expressly incorporated by reference.

Once a TRPM4 nucleic acid is identified, it can be cloned and, if necessary, its constituent parts recombined to form the entire TRPM4 gene. Once isolated from its natural source, e.g., contained within a plasmid or other vector or excised therefrom as a linear nucleic acid segment, the recombinant TRPM4 nucleic acid can be further used as a probe to identify and isolate other TRPM4 nucleic acids, from other multicellular eukaryotic organisms, for example additional coding regions. Recombinant TRPM4 nucleic acids can also be used as a "precursor" nucleic acids to produce modified or variant TRPM4 nucleic acids.

In another embodiment, the TRPM4 nucleic acid (e.g., cDNA or genomic DNA), as described above, encoding the TRPM4 polypeptide can be inserted into a replicable vector for cloning (amplification of the DNA) or for expression using techniques known in the art, as disclosed for example in Sambrook et al., *Molecular Cloning* (2000), which is incorporated herein by reference in its entirety. Various vectors are publicly available and may be in a number of configurations, for example, in the form of a plasmid, cosmid, viral particle, or phage. The appropriate nucleic acid sequence may be inserted into the vector by a variety of procedures, using techniques known in the art. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

A host cell comprising such a vector is also provided. By way of example, the host cells may be mammalian host cell lines which include Chinese hamster ovary (CHO), COS cells, cells isolated from human bone marrow, human spleen or kidney cells, cells isolated from human cardiac tissue, human pancreatic cells, human leukocyte, monocyte cells, insulin-secreting, cells, including but not limited to pancreatic β-cells. INS-1, and βTC-3 cells. More specific examples of host cells include monkey kidney CV1 line transformed by SV40 (COS-7, ATCC CRL 1651); human embryonic kidney line (293 or 293 cells subcloned for growth in suspension culture, Graham et at., *J. Gen Virol.*, 36:59 (1977)); Chinese hamster ovary cells/-DHFR (CHO, Urlaub and Chasin, *Proc. Natl. Acad. Sci. USA,* 77:4216 (1980)); human pancreatic β-cells; mouse sertoli cells (TM4, Mather, *Biol. Reprod.,* 23:243-251 (1980)); human lung cells (W238, ATCC CCL 75); human liver cells (Hep G2, HB 8065); and mouse mammary tumor cells (MMT 060562, ATCC CCL51). The selection of the appropriate host cell is deemed to be within the skill in the art. In the preferred embodiment, HEK-293 cells are used as host cells. A process for producing TRPM4 polypeptides is further provided and comprises culturing host cells under conditions suitable for expression of the TRPM4 polypeptide and recovering the TRPM4 polypeptide from the cell culture.

In another embodiment, expression and cloning vectors are used which usually contain a promoter, either constitutive or inducible, that is operably linked to the TRPM4-encoding nucleic acid sequence to direct mRNA synthesis. Promoters recognized by a variety of potential host cells are well known. The transcription of a TRPM4 DNA encoding vector in mammalian host cells is preferably controlled by an inducible promoter, for example, by promoters obtained from heterologous mammalian promoters, e.g., the actin promoter or an immunoglobulin promoter and from heat-shock promoters. Examples of inducible promoters which can be practiced in the invention include the hsp 70 promoter, used in either single or binary systems and induced by heat shock; the metallothionein promoter, induced by either copper or cadmium (Bonneton et al., FEBS Lett. 1996 380(1-2): 33-38); the *Drosophila* opsin promoter, induced by *Drosophila* retinoids (Picking, et al., Experimental Eye Research. 1997 65(5): 717-27); and the tetracycline-inducible full CMV promoter. Of all the promoters identified, the tetracycline-inducible full CMV promoter is the most preferred. Examples of constitutive promoters include the GAL4 enhancer trap lines in which expression is controlled by specific promoters and enhancers or by local position effects (http://www.fruitfly.org; http/;/www.astorg.u-strasbg.fr:7081); and the transactivator-responsive promoter, derived from *E. Coli*, which may be either constitutive or induced, depending on the type of promoter it is operably linked to.

Transcription of a DNA encoding the TRPM4 by higher eukaryotes may be increased by inserting an enhancer sequence into the vector. Enhancers are cis-acting elements of DNA, usually about from 10 to 300 bp. that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the TRPM4 coding sequence, but is preferably located at a site 5' from the promoter.

Candidate Agents

The term "candidate agent" as used herein describes any molecule capable of binding to TRPM4, modulating the activity of a TRPM4 ion channel, altering the expression of TRPM4 within cells, and/or modulating insulin secretion by a cell. As described above, the activity of a TRPM4 ion channel includes its monovalent cation permeability, its translocation, and the kinetics of its electrical conductance.

A candidate agent molecule as described herein, can be an oligopeptide, small organic molecule, polysaccharide, polynucleotide, or multivalent cation etc. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are multivalent cations or organic molecules, or small organic compounds having a molecular weight of more than 100 and less than about 2,500 daltons (D). Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclic carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

In a preferred embodiment, candidate agents are potential or actual hypoglycemic agents, insulin analogs, or other types of molecules that may be "anti-diabetic" agents. Anti-diabetic agents comprise molecules and compositions which alleviate the symptoms of diabetes. Anti-diabetic agents can include sulfonylureas, biguanides, alpha-glucosidase inhibitors, thiazolidinediones, meglitinides, amino acid D-phenylalanine derivatives, amylinomimetics, incretin mimetics, DPP-4 inhibitors, insulin analogs, and combinations thereof.

In some embodiments the candidate agent is a sulfonylurea compound having the general structure:

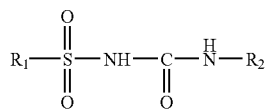

One subset of sulfonylurea compounds comprises the forgoing structure wherein $R_1$ is a substituted aryl and $R_2$ is an alkyl, cycloalkyl or substituted cycloalkyl.

Suitable non-limiting examples sulfonylurea compounds include, but are not limited to glipizide, gliclazide, glibenclamide, glimepiride, glyburide, chlorpropamide, tolbutamide, acetohexamide, tolazamide, and analogs, derivatives, prodrugs thereof.

Candidate agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate agents are proteins. By "protein" herein is meant at least two covalently attached amino acids, which includes proteins, polypeptides, oligopeptides and peptides. The protein maybe made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes amino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate agents are naturally occurring proteins or fragments of naturally occurring proteins. Thus, for example, cellular extracts containing proteins, or random or directed digests of proteinaceous cellular extracts, may be used. In this way libraries of multicellular eucaryotic proteins may be made for screening in the methods of the invention. Particularly preferred in this embodiment are libraries of multicellular eukaryotic proteins, and mammalian proteins, with the latter being preferred, and human proteins being especially preferred.

In a preferred embodiment, the candidate agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate agents are nucleic acids.

As described above generally for proteins, nucleic acid candidate agents may be naturally occurring nucleic acids, random nucleic acids, or "biased" random nucleic acids. For example, digests of procaryotic or eucaryotic genomes may be used as is outlined above for proteins.

In a preferred embodiment, the candidate agents are organic chemical moieties, a wide variety of which are available in the literature.

Assays of TRPM4 Channel Activity

As described above, the TRPM4 activity includes without limitation cation permeability, kinetics of conductance, gating, and translocation of the channel protein itself. In preferred embodiments, the invention provides assays which utilize methods of measuring and detecting TRPM4 channel activity.

In one embodiment, cation permeability and channel gating are monitored and quantified using a monovalent cation indicator. As used herein, a monovalent cation indicator is a molecule that is readily permeable to a cell membrane or otherwise amenable to transport into a cell e.g., via liposomes, etc. and upon entering a cell, exhibits a fluorescence that is either enhanced or quenched upon contact with a monovalent cation. Examples of monovalent cation indicators useful in the invention are set out in Haugland, R. P. *Handbook of Fluorescent Probes and Research Chemical.*, 6th ed. Molcular Probes, Inc Eugene, Oreg., pp. 504-550 (1996), incorporated herein by reference in its entirety.

In another embodiment, binding assays are used to screen for candidate agents which modulate TRPM4 and insulin secretion.

In a preferred embodiment for binding assays, either TRPM4 or the candidate agent is labeled with, for example, a fluorescent, a chemiluminescent, a chemical, or a radioactive signal, to provide a means of detecting the binding of the candidate agent to TRPM4. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound TRPM4. As known in the art, unbound labeled streptavidin is removed prior to analysis. Alternatively, TRPM4 can be immobilized or covalently attached to a surface and contacted with a labeled candidate agent. Alternatively, a library of candidate agents can be immobilized or covalently attached to a biochip and contacted with a labeled TRPM4. Procedures which employ biochips are well known in the art.

In a preferred embodiment, the ion permeabilty of TRPM4 is measured in intact cells, preferably HEK-293 cells, which are transformed with a vector comprising nucleic acid encoding TRPM4 and an inducible promoter operably linked thereto. Endogenous levels of intracellular ions are measured prior to inducement and then compared to the levels of intracellular ions measured subsequent to inducement. Fluorescent molecules such as fura-2 can be used to detect intracellular ion levels. TRPM4 permeability to $Na^+$, $K^+$, $Cs^+$ and to other monovalent cations are measured in such an assay. Candidate agents which modulate insulin secretion can be identified by their ability to modulate TRPM4 permeability as measured using the methods described herein.

In a preferred embodiment, candidate agents are identified which modulate expression levels of TRPM4 within cells. In some embodiments, these candidate agents wholly suppress the expression of TRPM4 within cells, thereby altering the cellular phenotype. In other embodiments, candidate agents enhance the expression of TRPM4 within cells, thereby altering the cellular phenotype. Examples of candidate agents which can affect expression levels of TRPM4 in cells include antisense cDNAs and DNAs, regulatory binding proteins and/or nucleic acids, as well as any of the other candidate agents herein described which modulate transcription or translation of nucleic acids encoding TRPM4.

In a further embodiment, the assays to screen for candidate agents affect TRPM4 activity by opening TRPM4 channels in a variety of cells such as cells of the nervous, immune, muscular systems of vertebrates, and insulin secreting cells, including but not limited to pancreatic β-cells, INS-1, and βTC-3 cells, wherein the opening of the TRPM4 channels results in a decreased or reduced immune response in vertebrates. Candidate agents such as the ones described herein are useful in the treatment of diseases, conditions associated with diseases, or disorders, such autoimmune or graft versus host diseases, or other related autoimmune disorders, wherein the decreased or reduced immune response results in an improved condition of the vertebrate (i.e., the disease, condition associated with the disease, or disorder is prevented, eliminated or diminished).

In still a further embodiment, candidate agents affect TRPM4 activity by closing TRPM4 channels in a variety of cells such as cells of the nervous, immune, muscular systems of vertebrates, and insulin-secreting cells, including but not limited to pancreatic β-cells, INS-1, and βTC-3 cells. Agents such as the ones described herein are useful in the treatment of diseases, conditions associated with diseases, or disorders such as breast and colon cancer, or other forms of cancer, wherein an enhanced or augmented immune response results in the improved condition of the vertebrate (i.e., the disease, condition associated with the disease, or disorder is prevented, eliminated or diminished).

The invention further relates to methods for identifying candidate agents that modulate the translocation of TRPM4 in a cell. In some embodiments the method comprises providing cell capable comprising a TRPM4 protein, contacting the cell with the candidate agent; and determining the effect of said candidate agent on the translocation of the TRPM4 protein. In some embodiments a candidate agent increases the translocation of the TRPM4 protein. In other embodiments a candidate agent decreases the translocation of the TRPM4 protein. In some embodiments, the method further comprises determining the level of TRPM4 protein in the presence of the candidate agent and comparing to the level of TRPM4 protein in the absence the candidate agent.

In some embodiments, TRPM4 can be conjugated with one or more marker molecule(s) to allow detection and quantification of TRPM4 expression and translocation. Suitable marker molecules include, but are not limited to, molecules that are detectable by spectroscopic, photochemical, radioactivity, biochemical, immunochemical, calorimetric, electrical, and optical means, including but not limited to, bioluminescence, phosphorescence, and fluorescence. Marker molecules include radioisotopes, epilope tags, affinity labels, enzymes, fluorescent groups, chemiluminescent groups, and the like. Marker molecules include molecules that are directly or indirectly detected as a function of their interaction with other molecule(s) as well as molecules detected as a function of their location or translocation. In some embodiments, the marker molecules are optically detectable marker molecules, including optically detectable proteins, such that they may be excited chemically, mechanically, electrically, or radioactively to emit fluorescence, phosphorescence, or bioluminescence. Optically detectable marker molecules include, for example, beta-galactosidase, firefly luciferase, bacterial luciferase, fluorescein, Texas Red, horseradish peroxidase, alkaline phosphatase, and rhodamine-conjugated antibody. In other embodiments, the optically detectable marker molecules are inherently fluorescent molecules, such as fluorescent proteins, including, for example, Green Fluorescent Protein (GFP).

Methods of detecting the intracellular location, concentration, or translocation of TRPM4 will vary depending upon the marker molecule(s) used. For example, the methods of detecting the intracellular location, concentration, or translocation of the TRPM4 and a marker molecules, including for example, the concentration of TRPM4 at a cell membrane, in endocytic vesicles or endosomes, and concentration of TRPM4 in clathrin-coated pits, and the like, will vary depending on the marker molecule(s) used. One skilled in the art readily will be able to devise detection methods suitable for the marker molecule(s) used. For optically marker molecules, any optical method may be used where a change in the fluorescence, bioluminescence, or phosphorescence may be measured due to a redistribution or reorientation of emitted light. Such methods include, for example, polarization microscopy, bioluminescence resonance energy transfer (BRET), fluorescence resonance energy transfer (FRET), evanescent wave excitation microscopy, and standard or confocal microscopy.

Detection for each of the items/events discussed herein could be conducted at one point in time, over a period of time, at two or more points in time for comparison (e.g., before and after exposure to a candidate agent), etc. An indication of the intracellular location, concentration, or translocation of TRPM4 could be determined by detecting for one or more of the items/events discussed herein in a cell exposed to the candidate agent and comparing the results to those obtained by detecting for the same item(s)/event(s) in a control cell, by comparing the results to a predetermined value or without reference to a predetermined level or a control cell.

Assays for Candidate Agents which Modulate Insulin Secretion

As discussed previously, TRPM4 plays a critical role in regulating the membrane potential of insulin secreting cells. As a result, assays which identify candidate agents that modulate TRPM4 activity and expression also identify candidate agents that modulate insulin secretion. Modulation of insulin secretion can also be directly detected and measured using methods known in the art.

In a preferred embodiment, the invention provides methods comprising two levels of screening for candidate agents. First, candidate agents which modulate TRPM4 activity and expression are identified among a pool of potential agents. Those agents which modulate TRPM4 activity and expression then form a second pool, and the candidate agents from this second pool are then contacted with an insulin secreting cell to determine if members of this second pool of candidate agents are able to modulate insulin secretion. In some circumstances, TRPM4-expressing cells are more easily obtained and manipulated than are insulin secreting cells. Thus, narrowing the field of potential candidate agents by first using TRPM4 activity and expression as a screen can streamline the process of identifying candidate agents which modulate insulin secretion.

Also provided herein are methods for screening for a candidate agent capable of modulating insulin secretion. In some embodiments the method comprises providing an insulin secreting cell comprising a TRPM4 protein, contacting the insulin secreting cell with a candidate agent, and detecting whether said agent modulates insulin secretion by the cell.

Methods for detecting insulin are well known in the art, such assays typically use ELISA or radioimmunoassay see for example, Bergsten and Hellman, 1993, Diabetes 42:670-4; U.S. Pat. Nos. 6,642,003 and 6,849,708 each of which is incorporated by references in its entirety.

Detection for insulin secretion could be conducted at one point in time, over a period of time, at two or more points in time for comparison (e.g., before and after exposure to a candidate agent), etc. An indication of modulating insulin secretion could be determined by detecting for one or more of the items/events discussed herein in a cell exposed to the candidate agent and comparing the results to those obtained by detecting for the same item(s)/event(s) in a control cell, by comparing the results to a predetermined value, or without reference to a predetermined level or a control cell. In a specific embodiment detecting comprises determining the amount of insulin secreted by said cell in the presence of said candidate agent and comparing to the amount of insulin secreted by said cell in the absence of said candidate agent.

Also provided herein are methods for screening for a candidate agent capable of modulating insulin secretion comprising providing an insulin secreting cell comprising a TRPM4 protein, contacting the insulin secreting cell with a candidate agent; contacting the insulin secreting cell with a compound to induce insulin secretion and detecting whether said agent modulates insulin secretion by the cell. As used herein the phrase "induce insulin secretion" means any compound which may induce insulin secretion when administered to cell. Examples of compounds which induce isulin secretion include, without limitation, glucose, arginine vasopressin (AVP), ATP, and analogs thereof as well as those compounds which are found to induce insulin secretion, whether in existence today or developed in the future.

EXAMPLES

Commercially available reagents referred to in the examples were used according to manufacturer's instructions unless otherwise indicated.

Example 1

Characterization of TRPM4 Currents in β-Pancreatic Cell

RT-PCR and Immunoprecipitation: Total RNA was extracted with RNAzol according to the manufacturer's protocol (ISO-TEX Diagnostics, Friendswood, Tex.). DNAse I-treated RNA was used for reverse transcription using RETROscript Kit (Ambion, Austin, Tex.). PCR was performed by a standard method using Advantage Polymerase PCR Kit (Clonetch, Palo Alto, Calif.). For immunoprecipitation, cells were lysed for 30 min at 4° C. in Tris buffer pH 7.5 containing 1% Triton X-100 (Bio-Rad, Hercules, Calif.) and protease inhibitors. Immunoprecipitation was resolved by 6% SDS-PAGE blotted with the rabbit polyclonal antisera against the C-terminal region of human TRPM4 and visualized by Enhanced Chemiluminescence (Amersham Pharmacia Biotech).

Figure 4A:
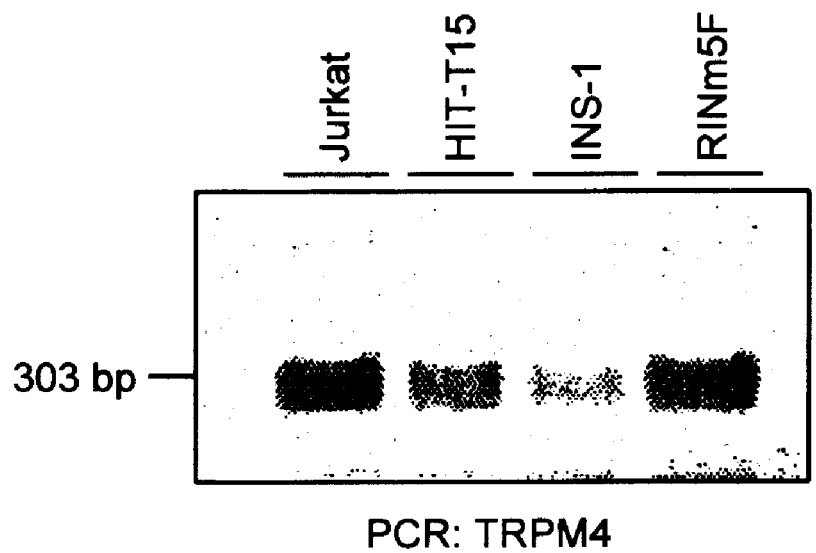
FIGS. 4A-G show the characterization of TRPM4 currents in pancreatic β-cells.

FIG. 4A shows the total RNA from different cell lines that was isolated and transcribed into cDNA. RT-PCR was performed with specific primers for TRPM4. TRPM4 transcripts were detected in HIT-T15 (hamster derived), INS-1 and RINm5F (rat derived) cells. The cDNA of Jurkat T cells were used as positive control (Launay P, et al. (2004) Science, 306, 1374-7.

Figure 4B:
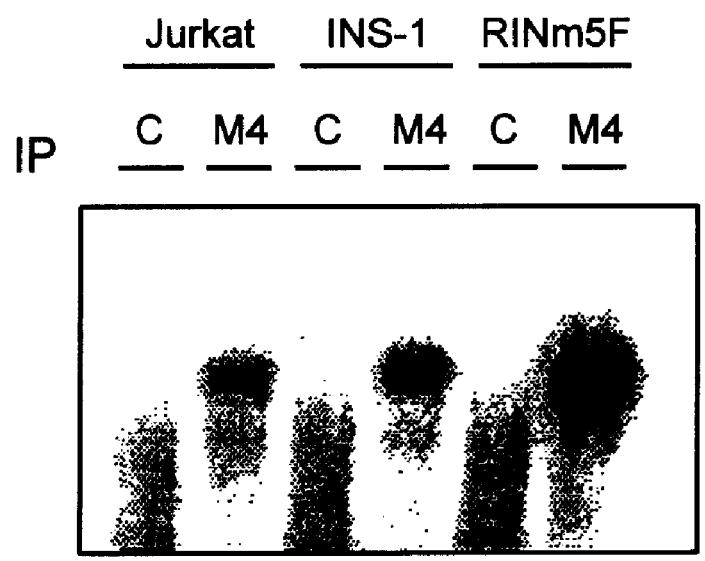

FIG. 4B shows detection of TRPM4 proteins. Cells were analyzed for expression of TRPM4 protein after immunoprecipitation/immunobloting with the polyclonal antibody against TRPM4 (M4). To confirm protein expression in the plasma membrane, rabbit polyclonal anti-peptide antibody against TRPM4 was used. The channel was detected in INS-1 and RINm5F cell lines and Jurkat T-cells as a single band with the predicted molecular size (FIG. 4B). No protein was detected after immunoprecipitation with an irrelevant control antibody (C).

Figure 4C:
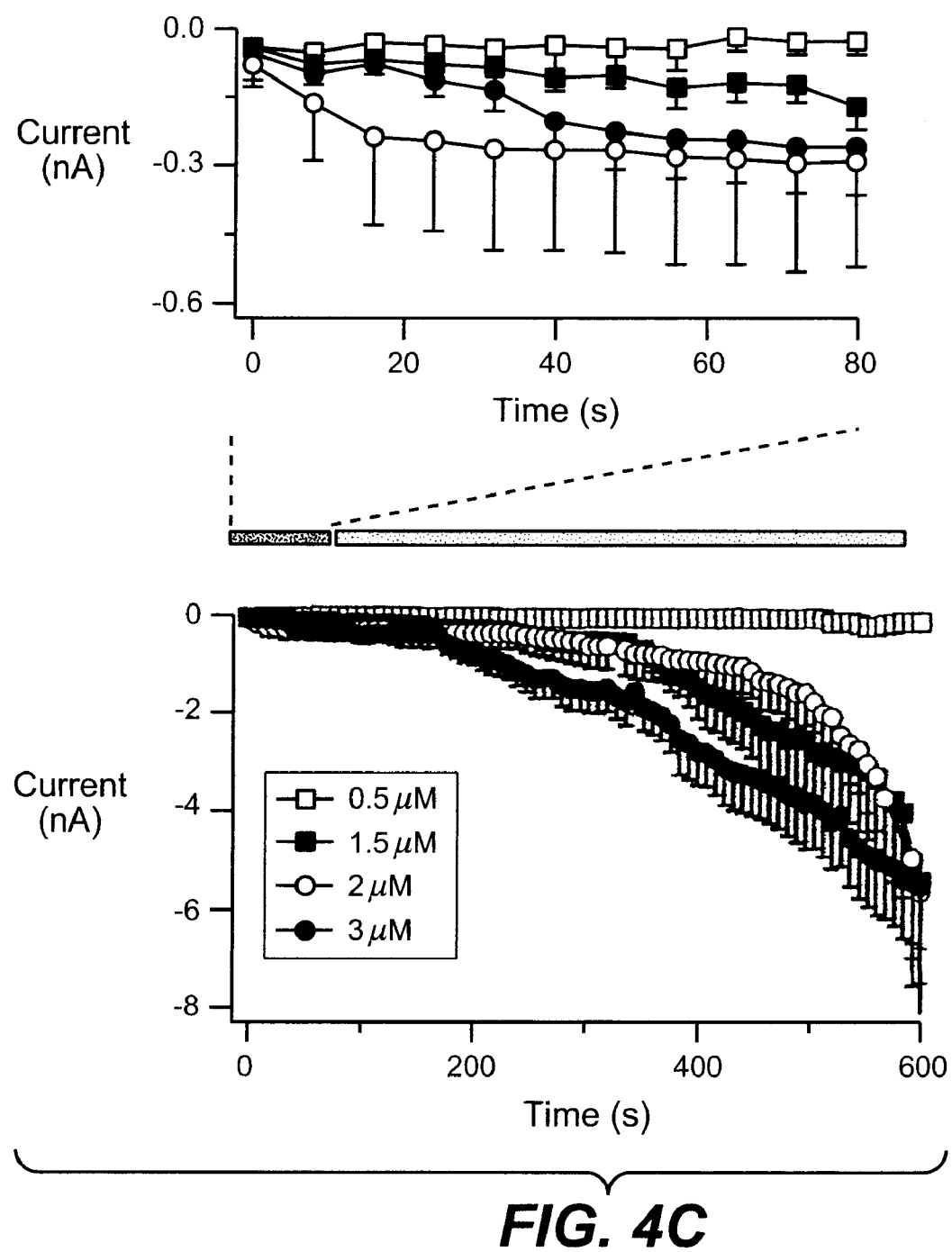
Figure 4D:
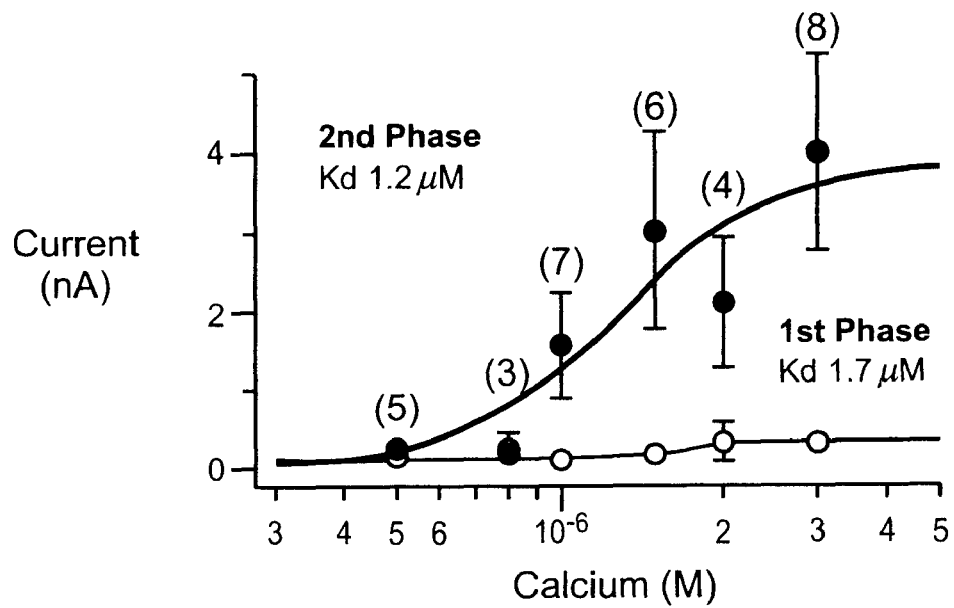
Figure 4E:
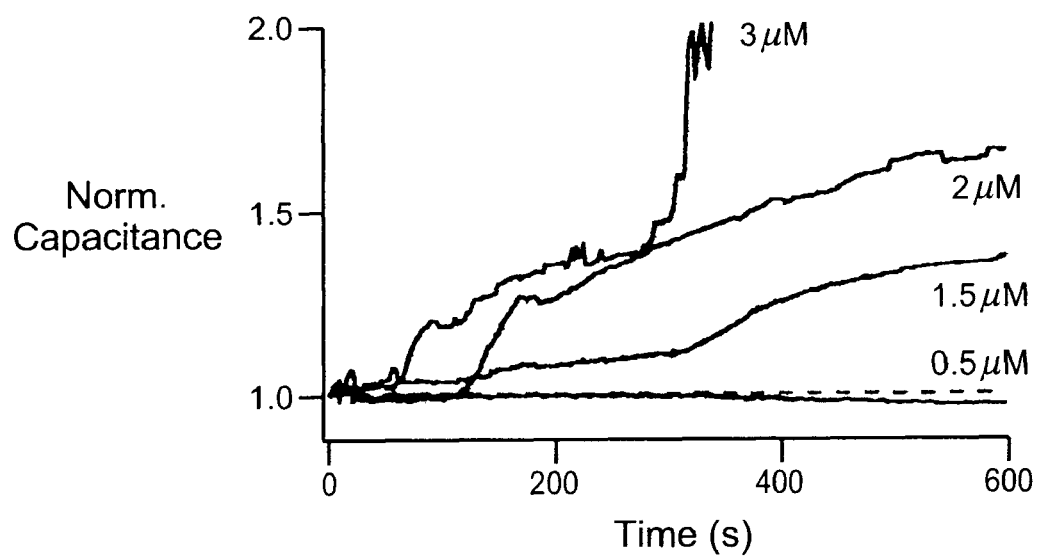
Figure 4F:
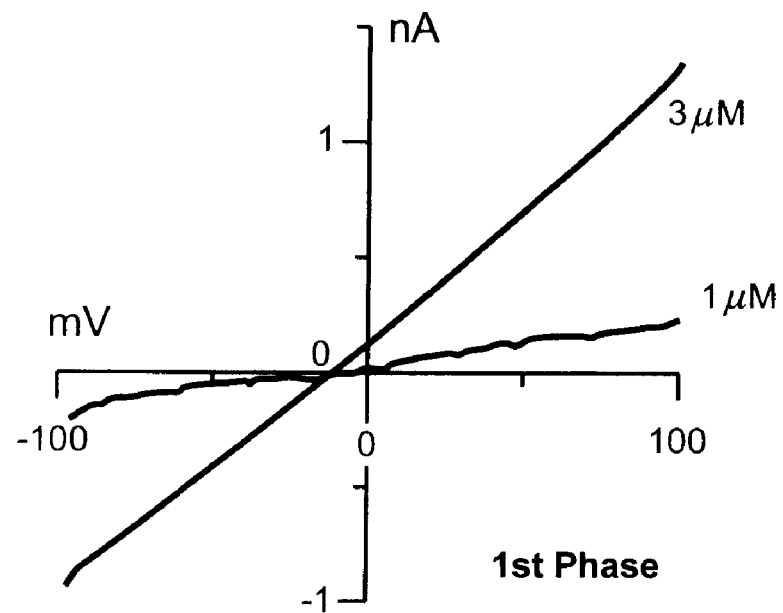
Figure 4G:
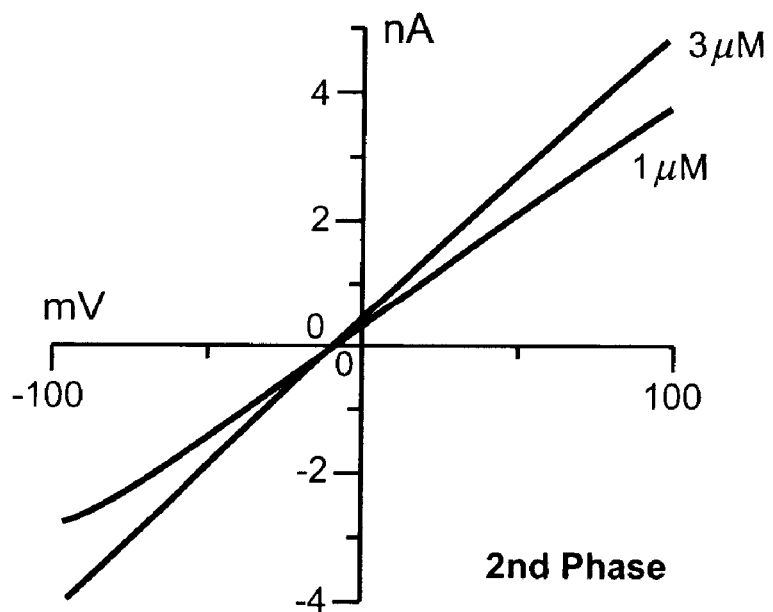

INS-1 cells were selected for the functional characterization, because they represent a widely accepted model for β-cell metabolism and insulin biosynthesis (Frodin M, et al. (1995) J Biol Chem, 270, 7882-9; Kennedy E. D, et al. (1996) J Clin Invest, 98, 2524-381 Merglen A, et al. (2004) Endocrinology, 145, 667-78). FIG. 4C Lower panel: show the average inward currents carried by TRPM4 from INS-1 cells (means±s.e.m.) extracted at −80 mV and +80 mV with $[Ca^{2+}]_i$ buffered between 0.5-3 μM. Perfusion of cells with 0.5-3 μM $[Ca^{2+}]i$ induced TRPM4 currents in a concentration-dependent manner (FIG. 4C) that typically exhibited a biphasic pattern. FIG. 4C upper panel shows the average inward currents showing the first phase during the initial 80 s after establishment of whole-cell configuration (n=4-7 cells/concentration). The first phase was observed within seconds after establishment of whole-cell configuration (FIG. 4C upper panel) and was followed by a secondary phase that gradually developed during the course of experiments (FIG. 4C lower panel). The current-voltage relationships taken from representative cells at the peak of the first phase and at 600 s for the second phase resemble those of TRPM4 (FIG. 4F and 4G). FIG. 4D show the dose-response curves for the first and second phase of TRPM4 activation with current amplitudes extracted at +80 mV either at 80 s (first phase) or 600 s into the experiment (second phase). A dose response fit to the first phase and secondary phase gave KD values of 1.7 μM and 1.2 μM, respectively (FIG. 4D). FIG. 4E shows the normalized capacitance changes from representative cells in FIG. 4C. Capacitance was normalized to the resting input capacitance measured immediately after break-in. Interestingly, the appearance of the secondary phase correlated with an increase in cell capacitance (FIG. 4E). FIG. 4F shows the current-voltage relationship under experimental conditions as described above, taken from a representative cell at the peak of the first phase. FIG. 4G shows the current-voltage relationship from representative cells taken at 600 s.

The above experiment was repeated in HIT-T15 β-cell model, as TRPM4 could be detected there by immunoprecipitation as well using the rabbit polyclonal anti-peptide antibody against TRPM4 (data not shown). In these cells we also observed a first phase and a secondary phase developing in parallel to an increase in cell size and comparable dose-response curves (data not shown).

Example 2

TRPM4 Suppression Affects Insulin Secretion

Measurement of insulin secretion: Truncated forms of TRPM4 cDNA were cloned into a modified version of the pCDNA4/TO vector with a N-terminal V5 epitope tag. The correct sequence of V5-ΔN-TRPM4 expression construct was confirmed by DNA sequencing. Constructs were transfected in INS-1 cells using Lipofectamine 2000™ and Plus Reagent™(Invitrogen, Carlsbad. Calif.) 24 hrs after cells were plated and experiments done 48-72 hrs post transfection. Control cells were transfected with reagents without the ΔN-TRPM4 DNA. INS-1 cells between p47-p55 were used in these experiments.

Static incubation experiments: INS-1 cells were plated into 24-well plates at 5×105 cells/well and grown for 3-4 days. Measurement of insulin secretion was accomplished by replacing the culture medium with modified KRB containing (in mM): NaCl 136, KCl 4.8, $CaCl_2$ 2.5, $KH_2PO_4$, 1.2, $MgSO_4$ 1.2, NaHCO3 5, HEPES 10, glucose 4 and 0.1% BSA, pH 7.4. After a 15-min equilibration period at 37 ° C., cells were exposed to different treatments and allowed to incubate for 15 min. At the end of each experiment, the KRB was collected for insulin RIA as previously described (Cheng H et al. (2002) Biochem J, 364, 33-9.) and the number of cells quantified. Each treatment was done in quadruplicates and repeated three times.

Perifusion experiments: The perifusion system used was as previously described (Cheng H et al. (2002)) with some modifications, INS-1 cells were grown on 22 mm round glass coverslips inside a multi-well culture plate for 3-4 days until confluency (~$10^6$ cells). Each coverslip was then removed from each well and mounted inside a 25 mm perifusion chamber (Millipore Swinnex Filter Holders, Waters, Milford, Mass., U.S.A,) with cells facing inside the chamber. Initially, the cells were perifused for a 20 min equilibration period at 37° C. with modified KRB. The flow rate was adjusted to 0.5 ml/min prior to experiments and samples collected at 30 s intervals. At the end, the glass coverslips were removed from the chambers and the number of cells quantified. Insulin concentration from effluent samples were measured by RIA. Experiments were replicated three times with different cell passages. Results from insulin secretion experiments were analyzed using SAS PROC MIXED procedure and a randomized block design. There were two factors, treatment and block. Individual mean comparisons were performed using F test. The significance level was set at P<0.05.

A truncated form of TRPM4, lacking the first 177 amino acids in the N terminus, was used to obtain a dominant negative effect (ΔN-TRPM4) and investigated the role of TRPM4 on insulin secretion. The ability to this mutant form to associate with endogenous TRPM4 channels and suppress activity has been reported (Launay P, et al. (2004) Science, 306, 1374-7. FIG. 5 shows the effect of TRPM4 protein suppression on insulin secretion under static incubation conditions. Exposure of control, mock-transfected INS-1 cells to 4, 10 and 25 mM glucose stimulated insulin secretion in a concentration-dependent manner, where glucose at 25 mM resulted in a ~2.2-fold increase in secretion compared to basal 4 mM. Suppression of endogenous TRPM4 by the ΔN-TRPM4 construct significantly decreased the response to 25 mM glucose (P<0.05) compared to control cells (FIG. 5A) and glucose at 25 mM resulted in a much reduced ~1.3-fold increase in secretion compared to basal 4 mM in ΔN-TRPM4 cells.

The response to 1 μM arginine vasopressin (AVP) was significantly decreased (P<0.05) in ΔN-TRPM4 compared to control cells (FIG. 5B). In this experiment, the response to KCl or L-arginine did not differ. Control cells were transfected with reagents without the ΔN-TRPM4 DNA. Values are mean±s.e.m. (n=4 wells/treatment group from 3 different cell passages; *P<0.05 compared to same concentration).

In β-cells, oscillations in the membrane potential result in oscillations in $Ca^{2+}$ signals, because each depolarization opens VDCC's and $Ca^{2+}$ influx occurs. As a result, insulin is secreted in a pulsatile fashion. To investigate the impact of TRPM4 on the pulsatile secretion pattern, a perifusion system was used to measure secretion in response to a glucose stimulus in ΔNTRPM4 cells. TRPM4 suppression significantly decreased insulin secretion to 25 mM glucose compared to control, mock-transfected INS-1 cells (FIG. 5C). INS-1 cells were perfused for 10 min with KRB containing 4 mM glucose to obtain a basal level and stimulated with 25 mM glucose for 20 min to induce insulin secretion. The typical oscillations observed with glucose stimulation were absent in ΔN-TRPM4 cells. At the end, cells were depolarized with 20 mM KCl to test their viability. Control cells were transfected with reagents without the ΔN-TRPM4 DNA. Experiments represents mean±s.e.m. (n=3/group from 3 different cell passages).

Example 3

Calcium-induced Exocytosis and TRPM4 Activation in HEK293 Cells

Electrophysiology: HEK293 cells grown on glass coverslips were transferred to the recording chamber and kept in a standard modified Ringer's solution of the following composition (in mM): NaCl 140, KCl 2.8, $CaCl_2$ 1, $MgCl_2$ 2, glucose 10, 1Hepes·NaOH 10, pH-7.2. with osmolarity adjusted to around 300 mOsm. For experiments with INS-1 cells, the external solution was further supplemented with 300 nM TTX, 100 μM 4,4-(TEA). Intracellular pipette-filling solutions for HEK293 cells contained (in mM): K-glutamate 140, NaCl 8, $MgCl_2$ 1, K-BAPTA 10, HEPES·KOH. pH 7.2 adjusted with KOH. The internal solution for INS-1 cells contained (in mM): Cs-glutamate 140, NaCl 8, MgCl2 1, Cs-BAPTA 10, HEPES·CsOH, pH 7.2 adjusted with CsOH. In experiments where $[Ca^{2+}]i$ was buffered to elevated levels. $CaCl^2$ was added as necessary (calculated with WebMaxC http:www.stanford.edu/~cpatton/webmaxcS.htm). Solution changes were performed by bath perfusion for calcium imaging experiments.

Patch-clamp experiments were performed in the tight-seal whole-cell configuration at 21-25 ° C. High-resolution current recordings were acquired by a computer-based patch-clamp amplifier system (EPC-9, HEKA, Lambrecht, Germany). Patch pipettes had resistance between 3-6 MΩ after filling with the standard intracellular solution. Immediately following establishment of the whole-cell configuration, voltage ramps of 50 ms duration spanning the voltage range of −100 to +100 mV were delivered from a holding potential of 0 mV at a rate of 0.5 Hz over a period of 600 to 1000 s. All voltages were corrected for a liquid junction potential of 10 mV between external and internal solutions when using glutamate as intracellular anion. Currents were filtered at 2.9 kHz and digitized at 100 μs intervals. Capacitive currents and series resistance were determined and corrected before each voltage ramp using the automatic capacitance compensation of the EPC-9. The low-resolution temporal development of membrane currents was assessed by extracting the current amplitude at −80 mV or +80 mV from individual ramp current records. Data analysis, statistical analysis and graphical display of patch-clamp experiments were done using the Igor Pro 5 software program (Wavemetrics).

Electrophysiological recordings of TRPM4 currents in β-cells showed a biphasic pattern during perfusion with elevated $Ca^{2+}$. The first phase activated within seconds after establishment of whole-cell configuration (Launay P. et al. (2002) Cell, 109, 397-407). Based on its rapid kinetics, it was investigated whether the first phase was due to activation of TRPM4 channels already present in the plasma membrane and that the secondary phase resulted from translocation and incorporation of TRPM4-containing vesicles to the plasma membrane during exocytosis. It was observed that an increase in cell capacitance correlated with the development of the secondary phase. To characterize the secondary phase, Trex-HEK-293 cells over-expressing TRPM4 were used to facilitate the visualization of currents/capacitance changes under different $[Ca^{2+}]i$ concentrations.

Figure 6A:
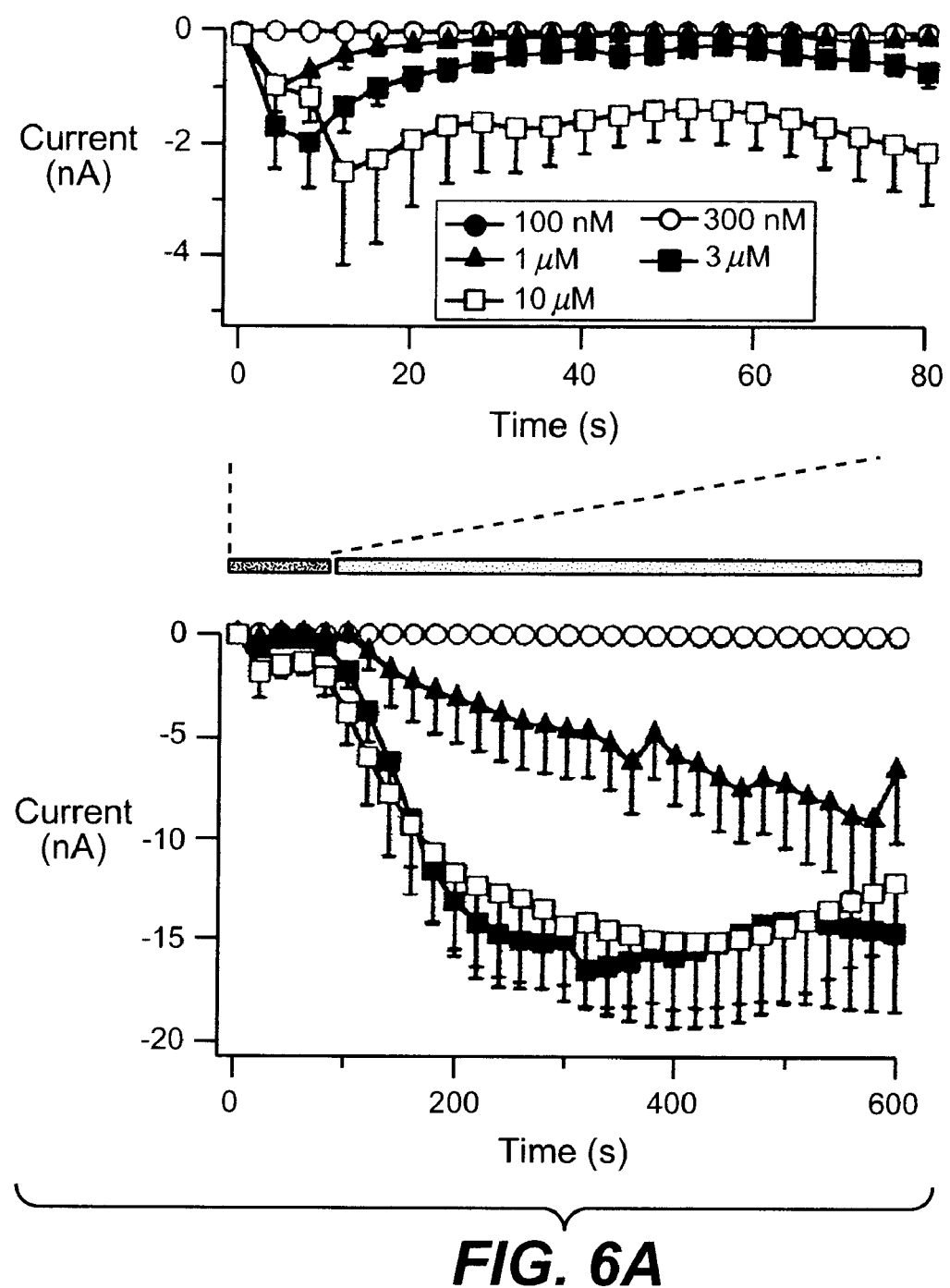
FIGS. 6A-F show calcium-induced exocytosis and TRPM4 activation in HEK293 cells.
Figure 6B:
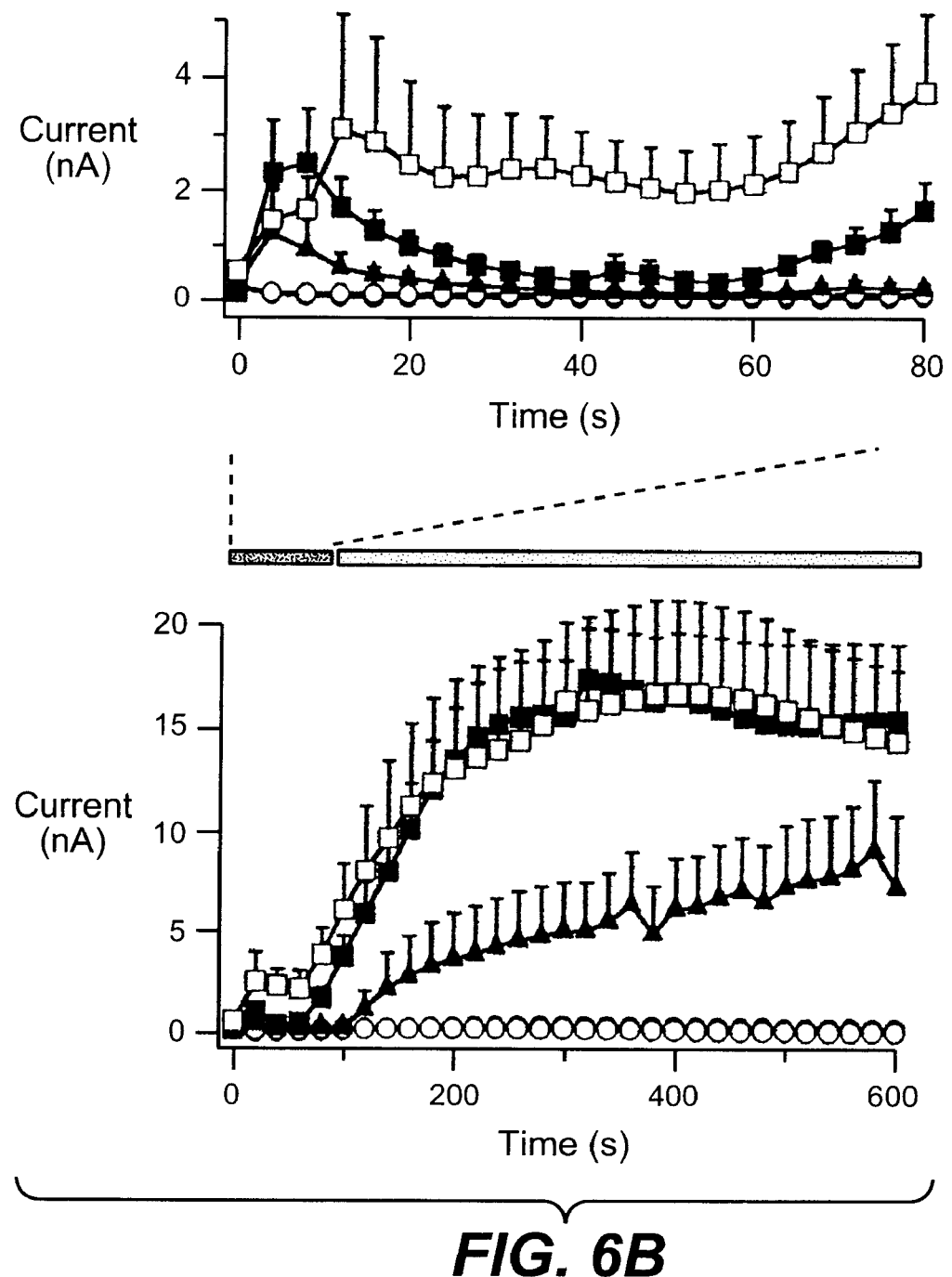

In agreement with the observations in β-cells, perfusion with 0.1-10 μM $[Ca^{2+}]_i$ induced biphasic currents in a concentration dependent manner (FIGS. 6A and 6B). The first phase was observed within seconds after establishment of the whole-cell configuration followed by a secondary phase that gradually developed during the course of experiments. FIG. 6A lower panel shows the average inward currents measured in 1TrexHEK-293 cells overexpressing TRPM4 (flag-TRPM4-TrexHEK293) at −80 mV where $[Ca^{2+}]_i$ buffered between 0.1-10 μM (mean±s.e.m., n=5-7 cells/concentration). FIG. 6A upper panel shows the average inward currents showing the first phase during the initial 80 s after establishment of whole-cell configuration. Note the development of the first phase during the initial 80 s of experiments, followed by a secondary phase that is associated with increased cell capacitance (see panel FIG. 6D). FIG. 6B lower panel shows the average outward currents at +80 mV carried by TRPM4 from the same cells as in (FIG. 6A). FIG. 6B upper panel shows the average outward currents during the initial 80 s after establishment of whole-cell configuration.

Figure 6C:
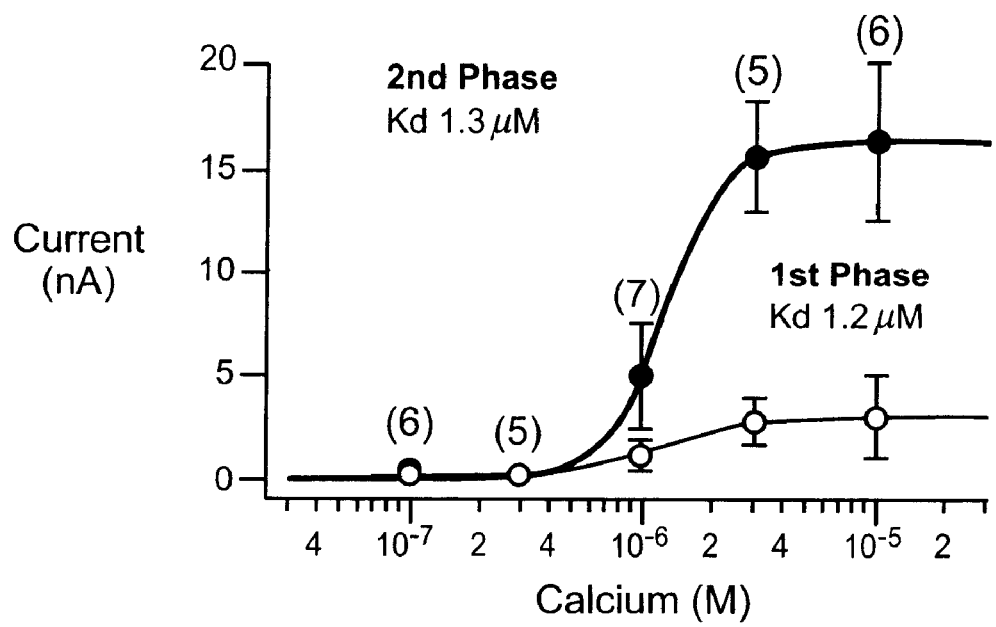
Figure 6D:
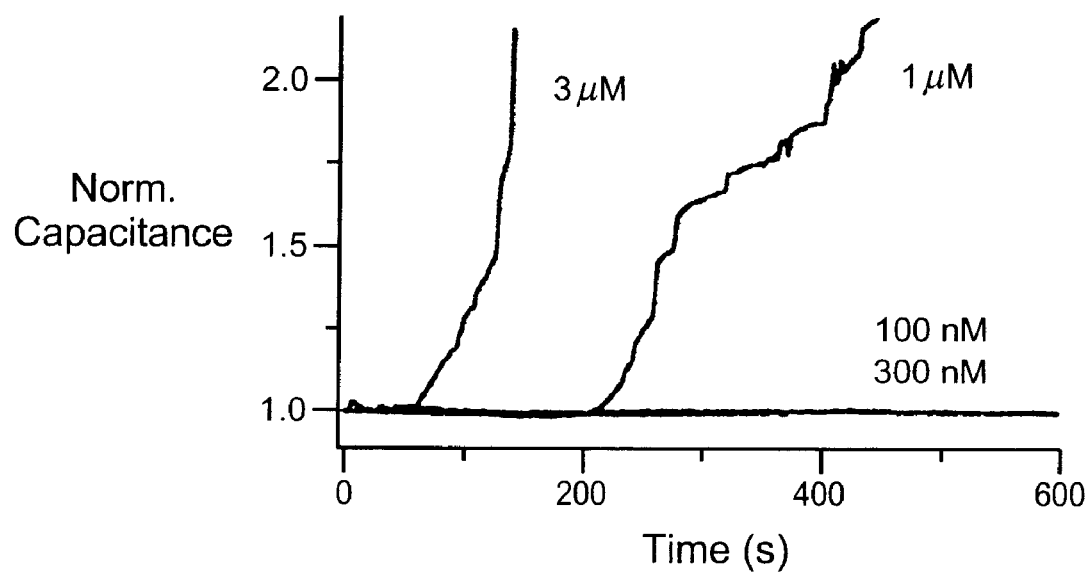
Figure 6E:
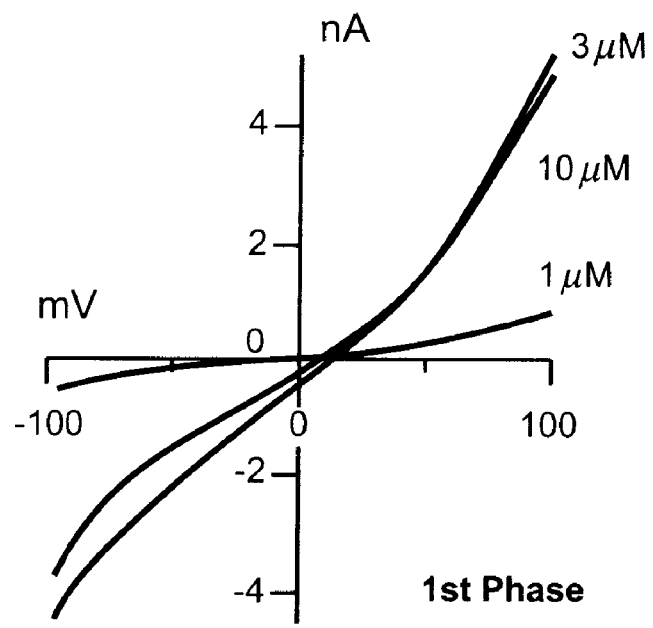
Figure 6F:
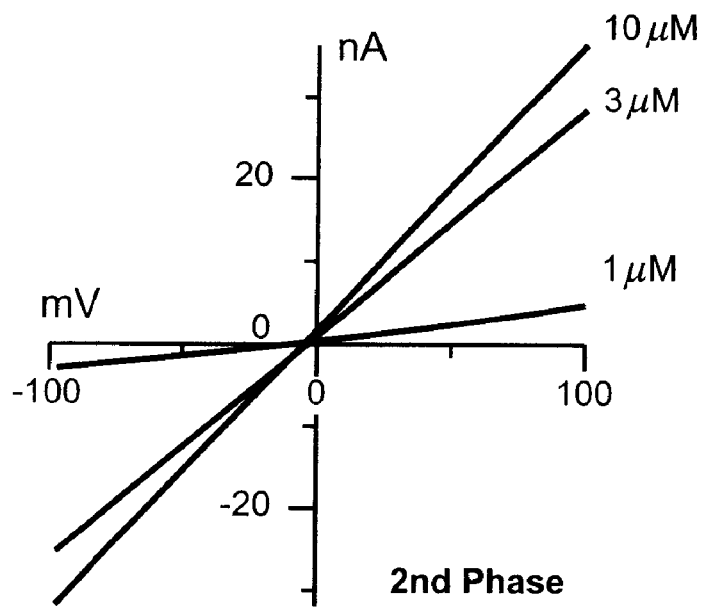

The current-voltage relationships taken from representative cells at the peak of the first and secondary phases for different $Ca^{2+}$ concentrations are typical of TRPM4 (FIGS. 6E and 6F). FIG. 6E shows the current-voltage relationship under experimental conditions as described above, taken from representative cells at the peak of the first phase during the initial 80 s of experiments. FIG. 6F shows the current-voltage relationship from the same cells as in (FIG. 6E) extracted at 600 s of experimental time.

FIG. 6C shows the dose-response curves for the first and second phase of TRPM4 activation with current amplitudes extracted at +80 mV either at the peak of the first phase, or 600 s into the experiment (second phase). A dose-response fit to the first phase and secondary phase gave $K_D$ values of 1.2 μM and 1.3 μM, respectively (FIG. 6C). FIG. 6D shows the normalized capacitance changes from representative cells. As in the β-cells, the appearance of the secondary phase also correlated with an increase in cell capacitance (FIG. 6D).

Example 4

Stimulation of Exocytosis Results in FM1-43 Dye Loss and Development of the Secondary Phase To test whether the secondary phase was due to exocytosis, intracellular vesicles were labeled with the membrane marker styryl dye FM1-43, which is used as fluorescent probe for membrane trafficking (Cochilla A J. et al. (1999) Annu Rev Neurosci. 22, 1-10: Smith C B. et al. (1996) Nature, 380, 531-4.). Cells were loaded with 10 μM FM1-43 for 24 hrs in culture medium and prior to experiments were washed and equilibrated for 15 min in standard buffer solution. Fluorescence of FM1-43 was excited with 480 nm and collected at 535 nm. Data acquisition from $Ca^{2+}$ measurement experiments were obtained with a dual excitation fluorometric imaging system (TILL-Photonics, Gräfelfingen, Germany) and controlled by TILLvisION software. Fura-2 AM loaded cells (5 μM/30 min/37° C.) were excited by wavelengths of 340 and 380 nm. Fluorescence emissions of several cells were sampled at 1 Hz and computed into relative ratio units of the fluorescence intensity of the different wavelengths. Data analysis, statistical analysis and graphical display of imaging data were done using the Igor Pro 5 software program (Wavemetrics).

FIG. 7 shows the stimulation of exocytosis results in FM1-43 dye loss and development of the secondary phase. FIG. 7A is the representative fluorescence images of flag-TRPM4-

Figure 7A:
FIGS. 7A-E show the stimulation of exocytosis results in FM1-43 dye loss and development of the secondary phase.
Figure 7B:
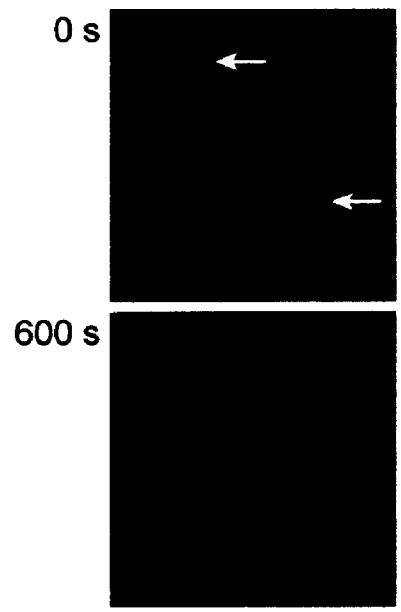
Figure 7C:
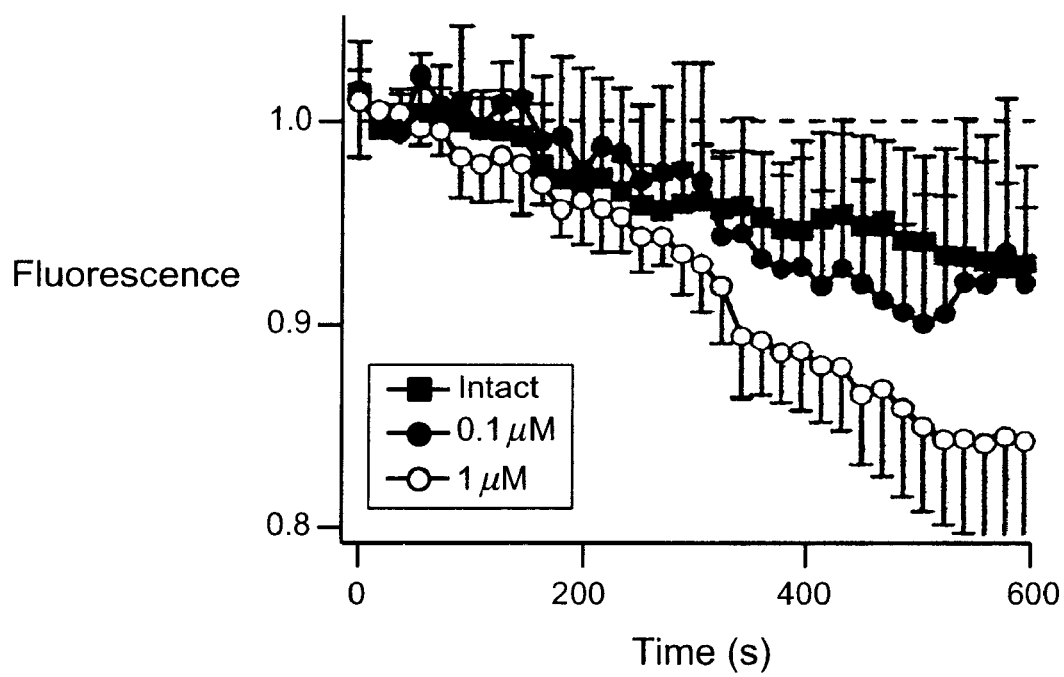

TrexHEK293 cells loaded with FM1-43 and perfused with 100 nM $Ca^{2+}$ (gray arrow) or control intact cells (white arrow) during 600 s. FIG. 7B shows cells perfused with 1 µM $Ca^{2+}$ (gray arrow) to induce exocytosis or control intact cell (white arrow) during 600 s. FIG. 7C is the average fluorescence loss (mean±s.e.m.) from cells perfused with 100 nM (n =3) or 1 µM $Ca^{2+}$ (n=6) and intact controls (n=9). Perfusion of cells with 1 µM $Ca^{2+}$ resulted in greater fluorescence loss compared to 100 nM or intact control cells (FIGS. 7A and 7B; average fluorescence changes in FIG. 7C).

Figure 7D:
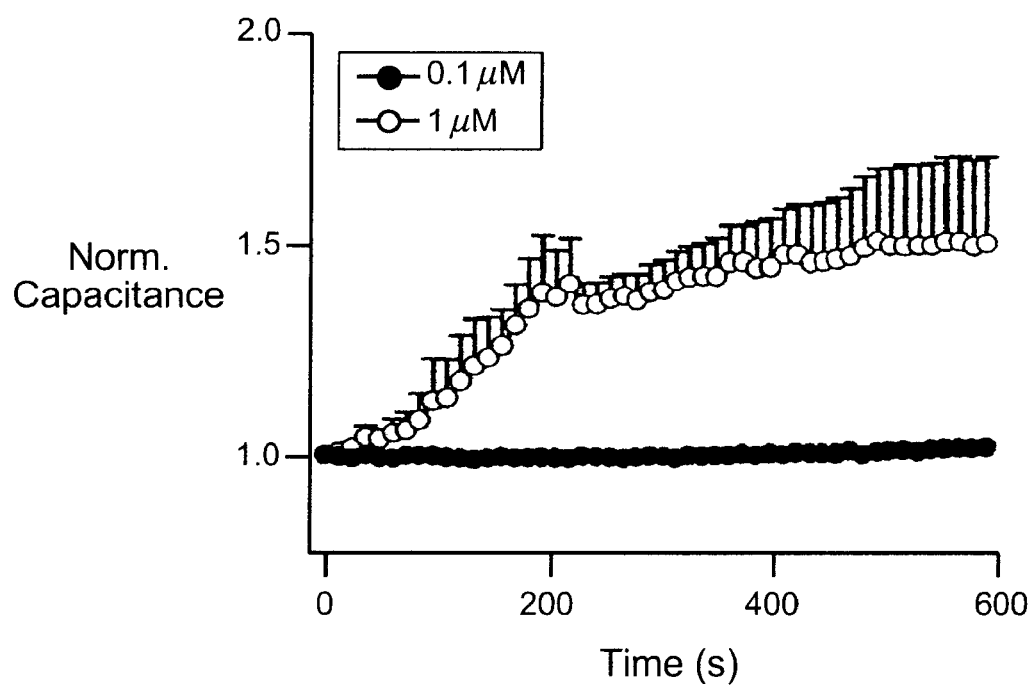
Figure 7E:
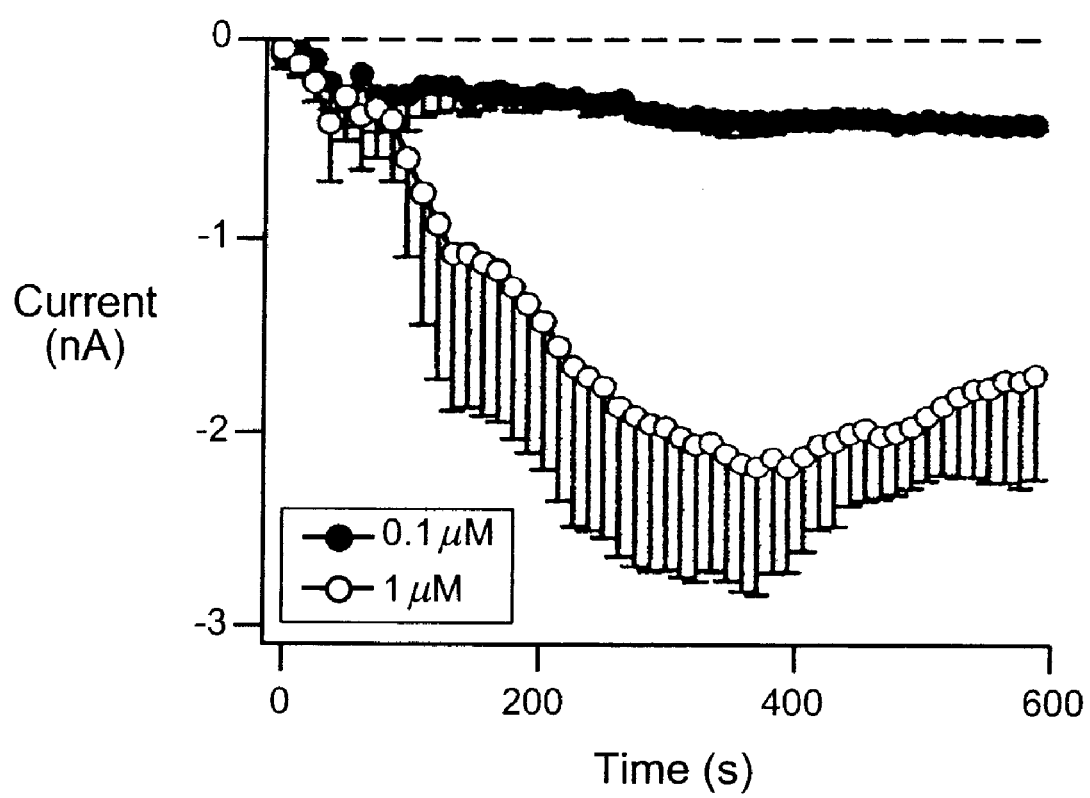

Electrophysiology recordings from cells loaded with FM1-43 dye were obtained to determine if there was an increase in capacitance during fluorescence loss. FIG. 7D is the average capacitance changes (mean±s.e.m.) from cells that were patched simultaneously with fluorescence measurements (n=3/group). Perfusion with 1 µM $[Ca^{2+}]i$ increased membrane capacitance (FIG. 7D) that correlated with the development of the secondary phase. This was not observed in cells perfused with 100 nM $[Ca^{2+}]i$ (FIG. 7E). FIG. 7E is the average inward currents carried by TRPM4 at −80 mV from same cells in FIG. 7D. These findings suggest that vesicles containing TRPM4 channels are recruited to the plasma membrane, since fluorescence loss and increased capacitance and the appearance of the secondary phase all correlated temporally.

Example 5

TRPM4 Translocation and Fusion with the Plasma Membrane

To visualize TRPM4 translocation, HEK-293 cells bearing a Flag-tagged version of TRPM4 were loaded with cytotracker green dye before stimulation with 1 µM ionomycin.

Figure 8A:
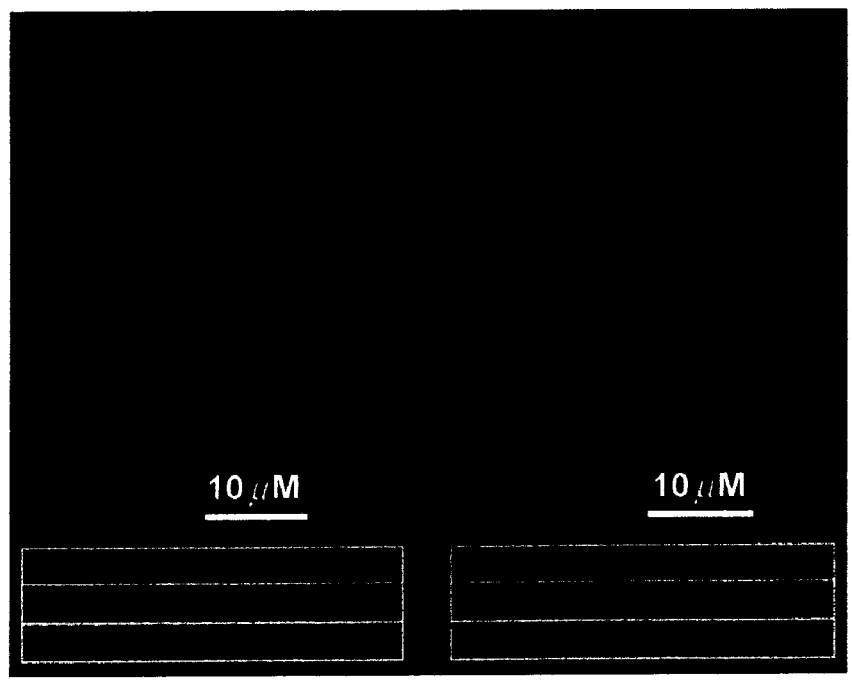
FIGS. 8A-C show TRPM4 translocation and fusion with the plasma membrane.

For confocal microscopy experiments exponentially growing Flag-TRPM4 transfected HEK-293 cells were plated on 12 mm glass coverslips and incubated overnight. After 24 hrs cells were incubated with 1 µM Cell Tracker Green (Molecular Probe, Eugene, Oreg.) during 30 min at 37° C. Cells were then activated with 1 µM ionomycin to induce exocytosis. The activation reaction was stopped and cells fixed by incubating coverslips in 100% methanol 10 min at −20° C. Cells were rinsed in PBS and incubated in blocking solution (PBS-0.5% FSG) for 45 min at room temperature to reduce nonspecific binding of antibodies. All subsequent steps were carried out at room temperature and coverslips rinsed 3 times in PBS-0.02% FGS. Primary and secondary antibodies were added sequentially for 30 min. The Flag antibody was used at 1/5000 and secondary antibody GAMAlexa 568 at 1/6500. Coverslips were then inverted into 10 ml of mounting medium containing antifade agents (Biomeda Corp., Foster City, Calif.). Confocal images were obtained using a Bio-Rad MRC 1024ES laser-scanning microscope (Bio-Rad, Hercules, Calif.), with Krypton/Argon laser FIG. 8A shows the cellular localization of flag-TRPM4, in resting flag-TRPM4-TrexHEK293 (left panels), and 1 µM ionomycin treated cells (right panels), stained for flag-TRPM4 expression (red) with 2.5 mg/ml mouse anti-Flag primary antibody (Sigma), and visualized using an Alexa-568 conjugated antimouse secondary antibody (Invitrogen). Cell bodies were delineated using 1 mM Cell Tracker (green) prior to fixing. Top panels are protected 7-stacked images taken at 0.65 mm increments through the cell, bottom panels are z-axis interpolated x-axis sections through the cell (Size bar=10 mm). Note the initial punctate localization of TRPM4 and shift of fluorescence to a plasma membrane localization following ionomycin treatment. Under confocal microscopy, the protected stacks showed a membrane translocation of TRPM4 (in red) after exocytosis (FIG. 8A).

Figure 8B:
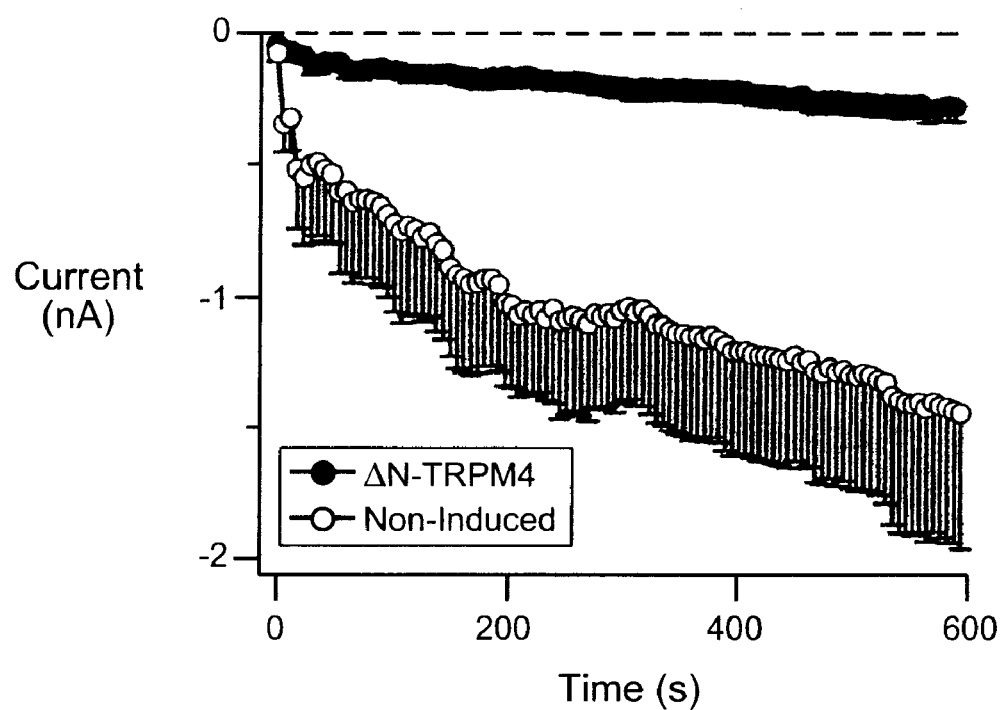
Figure 8C:
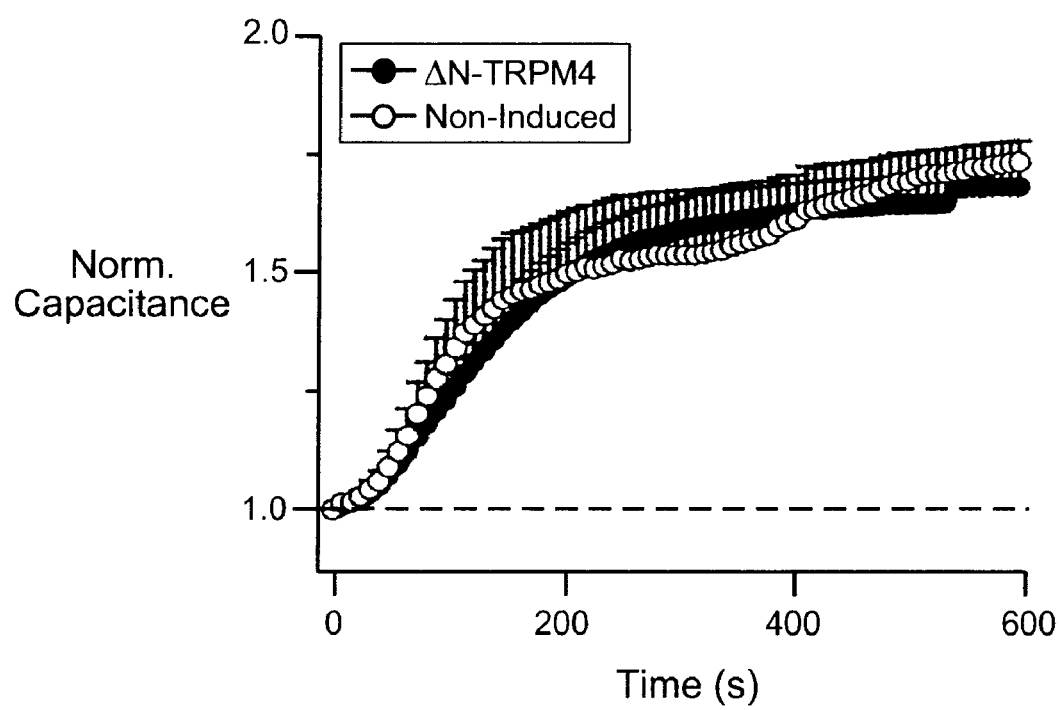

FIG. 8B is the average inward currents from ΔN-TRPM4 expressing cells (n=14) and non-tetracycline induced control cells (n=7) at −80 mV with $[Ca^{2+}]i$ buffered at 1 µM (mean±s.e.m.). HEK-293 cells expressing ΔN-TRPM4 constructs indeed had significantly smaller TRPM4 current amplitudes compared to controls when perfused with 1 µM $Ca^{2+}$ (FIG. 8B), however, there was no obvious effect on exocytosis as indicated by capacitance measurements (FIG. 8C). FIG. 8C shows the normalized capacitance changes from ΔN-TRPM4 expressing and control cells. These experiments indicate the inhibition of TRPM4 currents by a dominant negative, but does not alter exocytosis.

Example 6

Agonist-induced Secondary Phase in TRPM4 Current

Figure 9A:
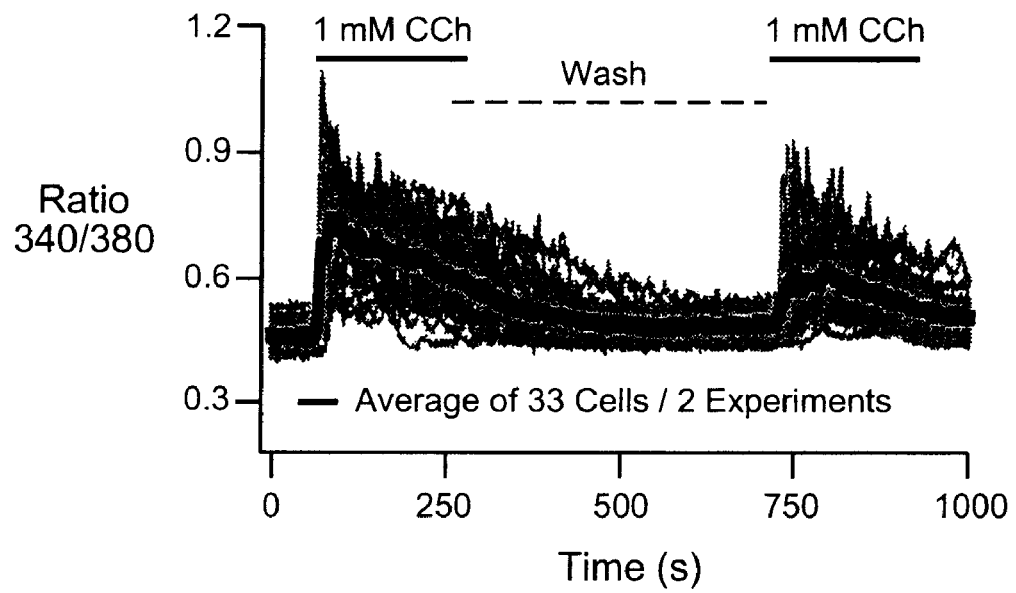
FIGS. 9A-D show agonist-induced secondary phase in TRPM4 current.
Figure 9B:
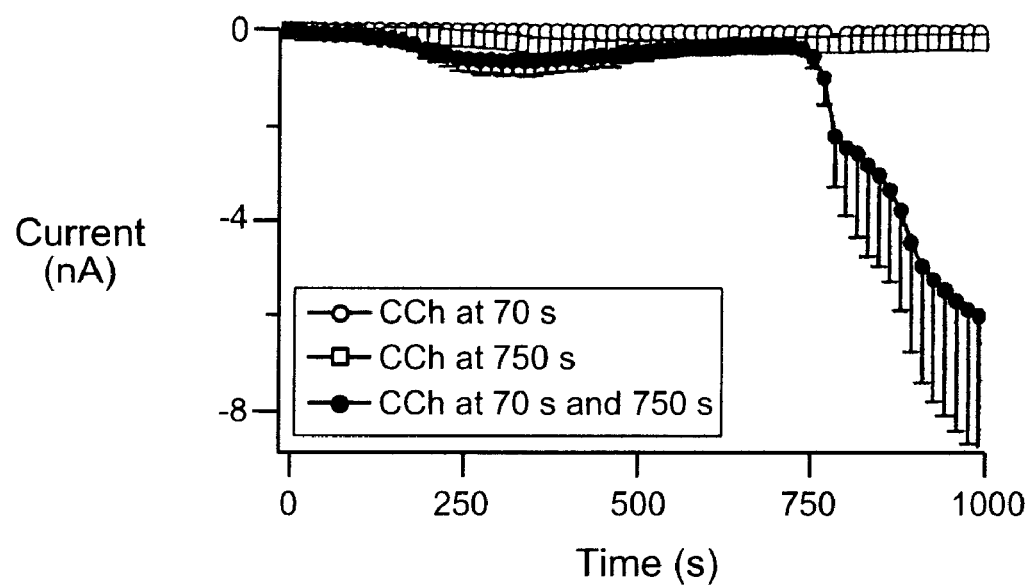

The fact that TRPM4 significantly reduced insulin secretion in response to glucose and AVP stimulation, the secondary phase of current recruitment with agonist stimulation was examined. FIG. 9A shows calcium measurement from Trex-HEK293 cells overexpressing TRPM4. Cells were treated with carbachol twice according to protocol used in the calcium measurement experiments (n=5). First, to induce exocytosis of TRPM4 containing vesicles and second to activate the new pool of TRPM4 present in the plasma membrane. Utilizing $Ca^{2+}$ imaging techniques, fura-2-AM loaded cells were stimulated with 1 mM carbachol for 200 s followed by washout and a second stimulation (FIG. 9A). The first carbachol application induced a sharp peak in $[Ca^{2+}]i$ that was followed by a sustained secondary phase due to $Ca^{2+}$ influx necessary for exocytosis and TRPM4 currents were less than 1 nA in amplitude. After a washout period, a second carbachol application resulted in a smaller $Ca^{2+}$ signal, however now the currents carried by TRPM4 were around 10 nA in amplitude. FIG. 9B is the average inward currents (mean±s.e.m.) carried by TRPM4 at −80 mV under unbuffered $Ca^{2+}$ conditions, The $Ca^{2+}$ response to carbachol is smaller during the second application, however, the currents generated due to increased TRPM4 at the plasma membrane are much larger. Control cells were treated with carbachol at 70 s (n=3) or 750 s (n=3). Control cells that received single carbachol stimulation failed to develop the secondary phase (FIG. 9B).

Figure 9C:
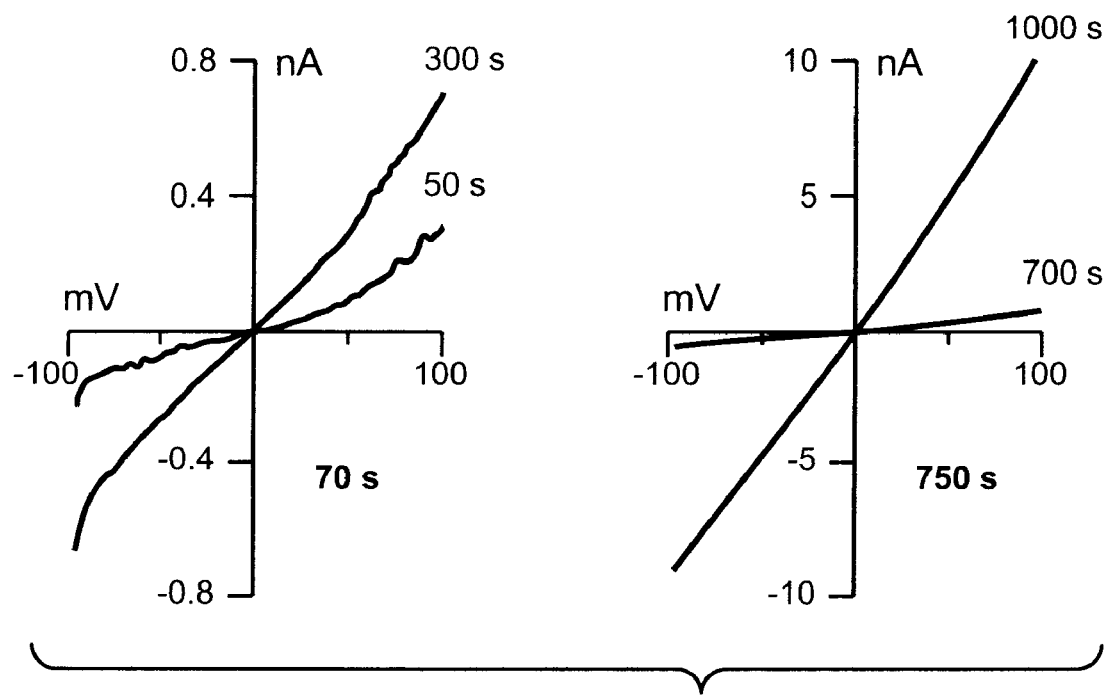
Figure 9D:
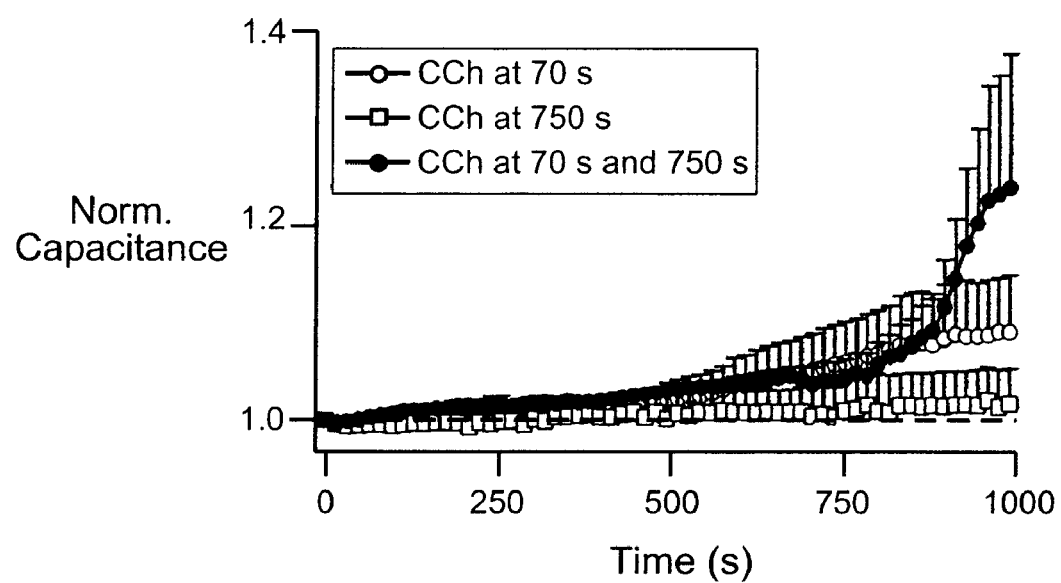

FIG. 9C is the current-voltage relationship typical of TRPM4 obtained from a representative cell (70 s and 750 s) that received double carbachol application. The current voltage relationships from a representative cell before and after carbachol stimulation for both time periods resemble those of TRPM4 (FIG. 9C). FIG. 9D is the average changes in capacitance from cells in FIG. 9B. In these experiments, exocytosis was confirmed by an increase in cell capacitance after carbachol stimulation (FIG. 9D).

Example 10

Glibenclamide Activates TRPM4 channels in INS and HEK293 cells

Figure 10A:
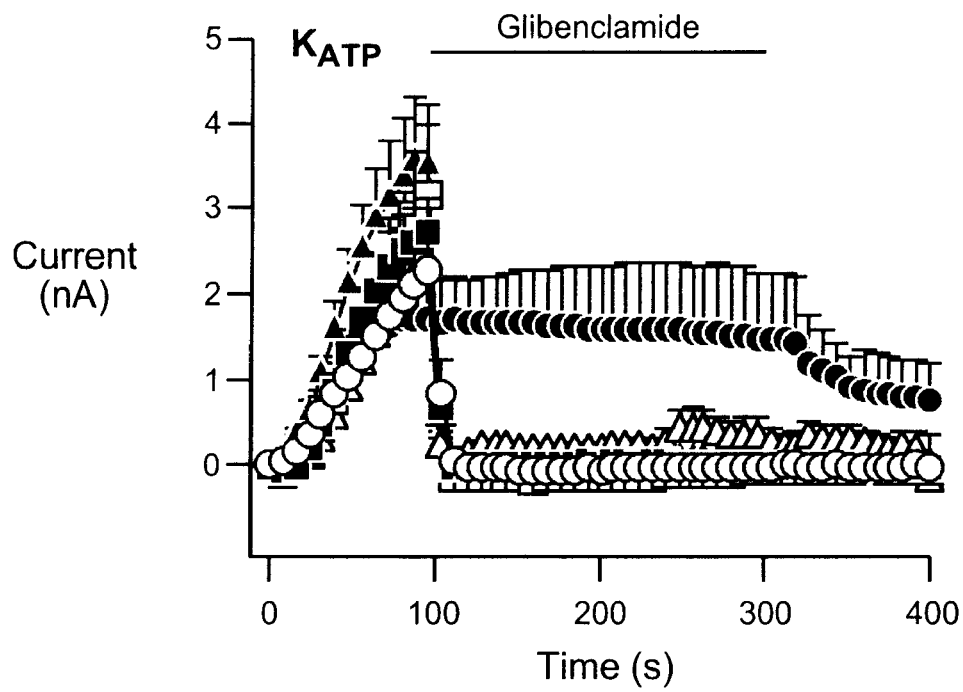
FIGS. 10A-E show the effects of glibenclamide on $K_{ATP}$ and TRPM4 currents in INS cells.
Figure 10B:
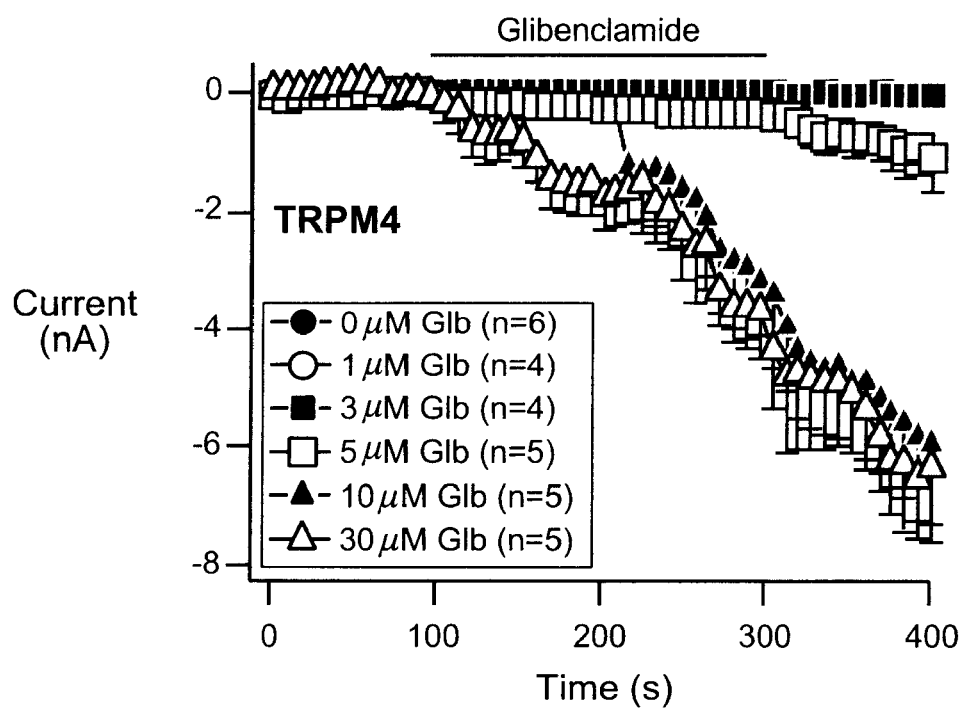
Figure 10C:
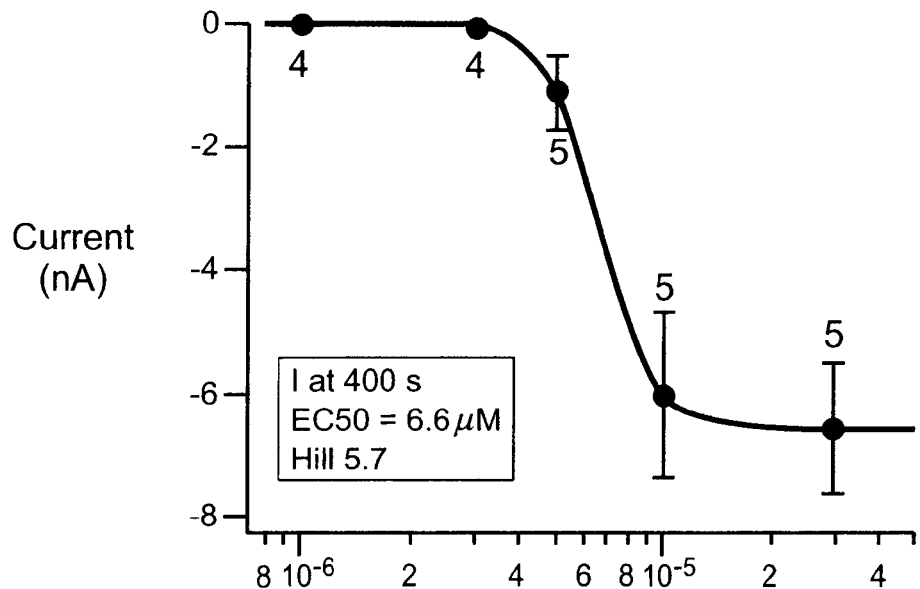
Figure 10D:
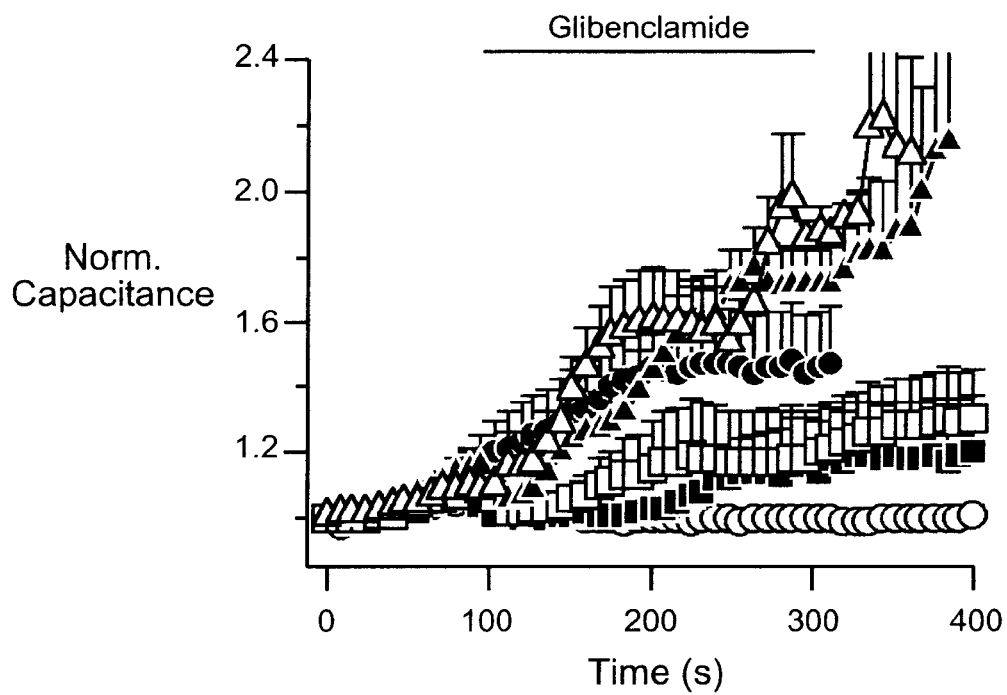
Figure 10E:
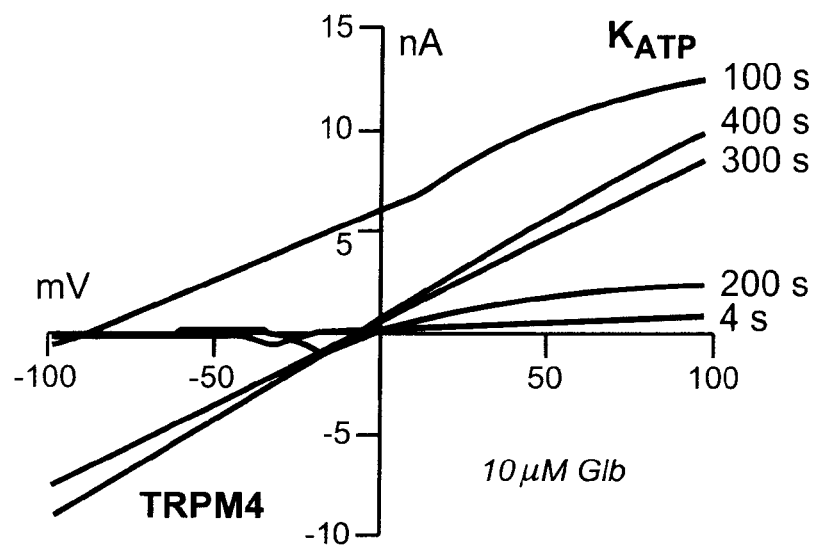
Figure 11A:
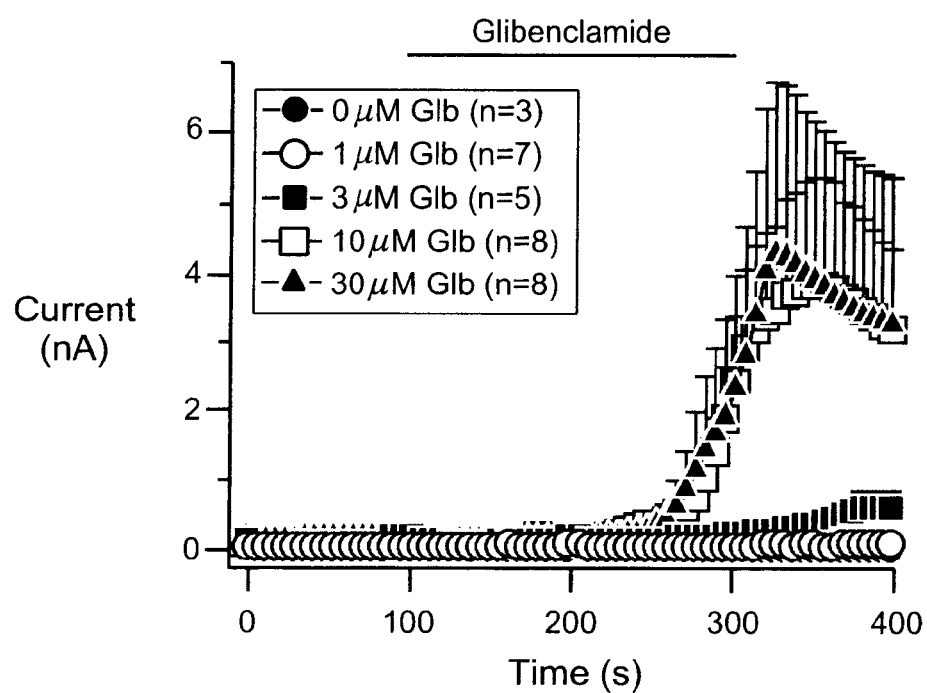
FIGS. 11A-E show the effects of glibenclamide on $K_{ATP}$ and TRPM4 currents in HEK293 cells.
Figure 11B:
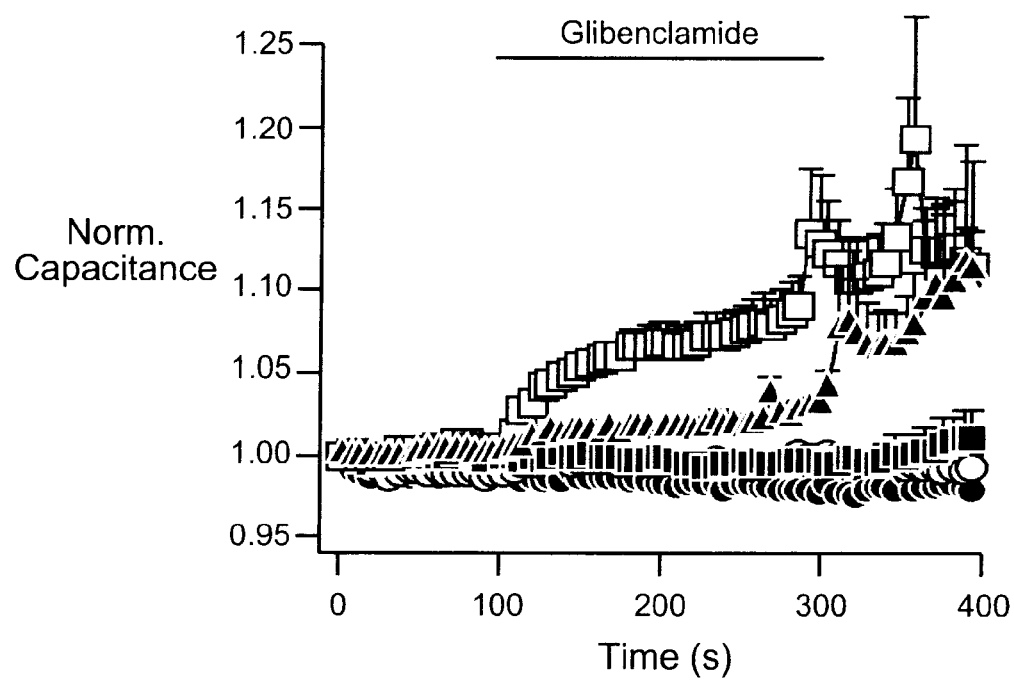
Figure 11C:
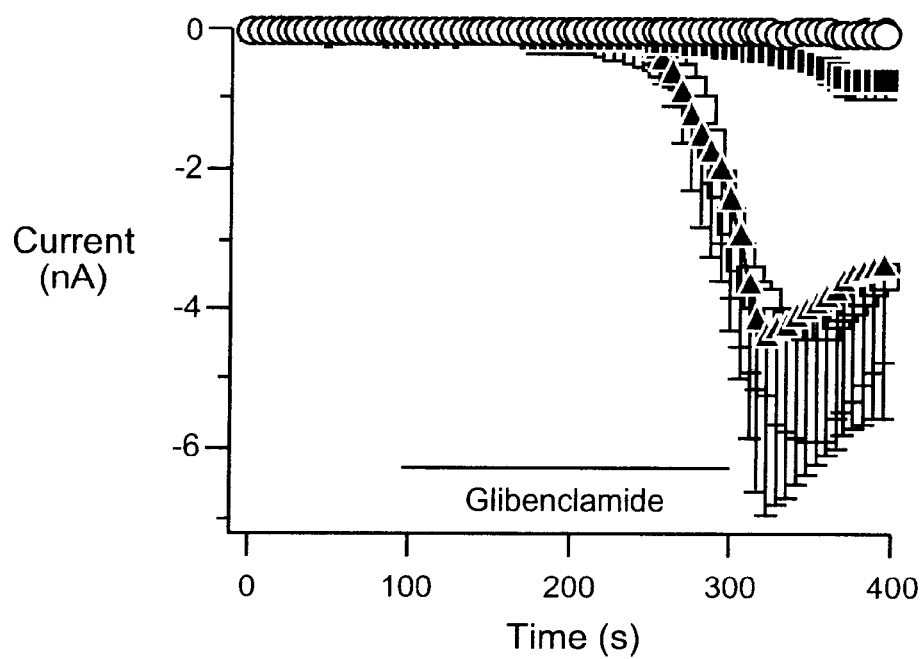
Figure 11D:
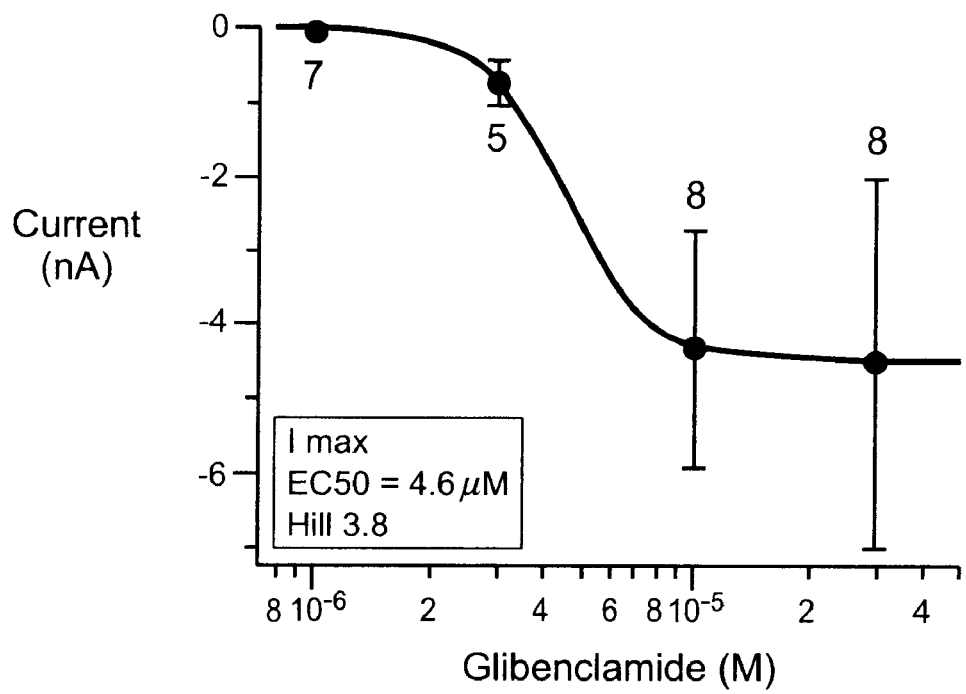
Figure 11E:
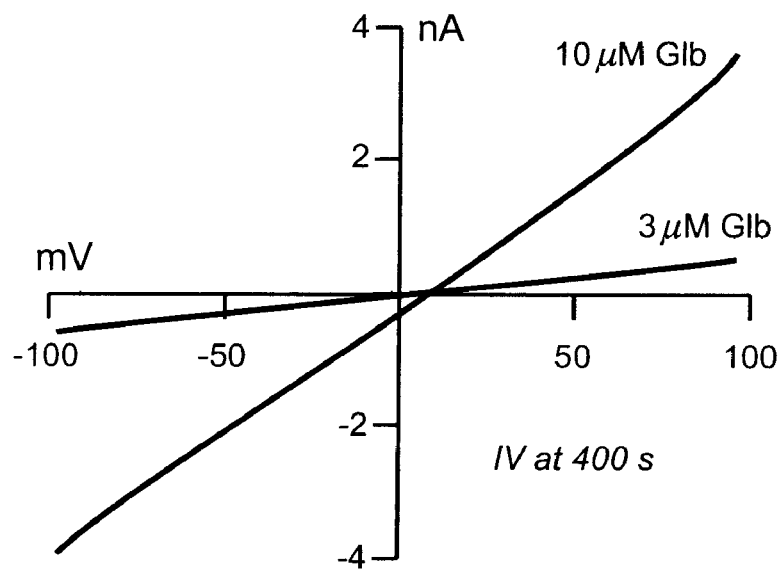

The sulfonylurea glibenclamide was tested on the activity of TRPM4 channels using the methods described herein. Glibenclamide was add to the external saline from a 100 mM stock solution in DMSO and pressure applied onto INS (FIG. 10) and HEK293 (FIG. 11) cells. Glibenclamide blocks ATP-dependent K channels (FIG. 10A) and activates TRPM4 channels (FIG. 10B) in the insulin-secreting rat beta cell line INS-1. INS cells are a model for pancreatic β-cells. Similar results were seen with TRPM4 channels expressed in HEK293 cells (FIG. 11).

What is claimed is:

1. A method of screening for modulators of insulin secretion comprising a) providing a cell, wherein said cell expresses a Transient Receptor Potential Melastatin 4 (TRPM4) channel;

b) identifying a candidate agent which modulates the activity of said TRPM4 channel;

c) contacting an insulin secreting cell with the candidate agent; and d) detecting modulation of insulin secretion of said insulin secreting cell by said candidate agent.

2. The method of claim 1, wherein said modulation comprises a change in the cationic permeability of said TRPM4 channel.

3. A method of screening for modulators of insulin secretion comprising
   a) contacting an insulin secreting cell with a candidate agent;
   b) detecting modulation of the cationic permeability of a Transient Receptor Potential Melastatin 4 (TRPM4) channel; and
   c) detecting modulation of insulin secretion.

4. The method of claim 1 or 3, wherein said candidate agent comprises a member selected from a sulfonylurea, a biguanide, an alpha-glucosidase inhibitor, a thiazolidinedione, a meglitinide, an amino acid D-phenylalaninederivative, an amylinomimetic, an incretin mimetic, a DPP-4 inhibitor, an insulin analog, and combinations thereof.

5. The method of claim 3, wherein said modulation of TRPM4 channel activity comprises a member selected from: modulation of monovalent cation permeability of said TRPM4 channel, modulation of translocation of said TRPM4 channel, modulation of expression of said TRPM4 channel, and combinations thereof.

6. A method of screening for modulators of Transient Receptor Potential Melastatin 4 (TRPM4) comprising
   a) contacting an insulin secreting cell expressing TRPM4 with a candidate agent; and
   b) detecting modulation of the cationic permeability of said TRPM4 channel.

* * * * *